United States Patent
Gelber

(10) Patent No.: US 7,691,376 B2
(45) Date of Patent: *Apr. 6, 2010

(54) OVARIAN CANCER CELL AND MYELOMA CELL SURFACE GLYCOPROTEINS, ANTIBODIES THERETO, AND USES THEREOF

(75) Inventor: Cohava Gelber, Hartsdale, NY (US)

(73) Assignee: ImmunoCellular Therapeutics, Ltd., Woodland Hills, CA (US)

( * ) Notice: Subject to any disclaimer, the term of this patent is extended or adjusted under 35 U.S.C. 154(b) by 22 days.

This patent is subject to a terminal disclaimer.

(21) Appl. No.: 11/753,221

(22) Filed: May 24, 2007

(65) Prior Publication Data

US 2007/0269372 A1 Nov. 22, 2007

Related U.S. Application Data

(60) Division of application No. 10/049,608, filed as application No. PCT/US00/21574 on Aug. 8, 2000, now Pat. No. 7,226,750, which is a continuation-in-part of application No. 09/374,367, filed on Aug. 13, 1999, now Pat. No. 6,376,654.

(51) Int. Cl.
*A61K 39/395* (2006.01)

(52) U.S. Cl. .............. 424/133.1; 424/138.1; 424/155.1; 424/174.1; 424/181.1; 424/183.1; 530/350; 530/387.1; 530/387.3; 530/391.3; 530/387.7; 530/388.8; 530/391.7

(58) Field of Classification Search .................. 530/530, 530/387.1, 387.3, 391.3, 387.7, 388.8, 391.7; 424/133.1, 138.1, 155.1, 174.1, 181.1, 183.1
See application file for complete search history.

(56) References Cited

U.S. PATENT DOCUMENTS 6,376,654 B1 * 4/2002 Gelber ..................... 530/388.8

FOREIGN PATENT DOCUMENTS

| WO | 88/03954 | 6/1988 |
|---|---|---|
| WO | 94/05329 | 3/1994 |
| WO | 96/26964 | 9/1996 |
| WO | 96/40295 | 12/1996 |

OTHER PUBLICATIONS

Greenspan et al. (Nature Biotechnology. 1999; 7: 936-937).*
Caldas et al. (Mol. Immunol. May 2003; 39 (15): 941-952).*
Stancoviski et al. (Proceedings of the National Academy of Science USA. 1991; 88: 8691-8695).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Jiang et al. (J. Biol. Chem. Feb. 11, 2005; 280 (6): 4656-4662).*
D. Avichezer et al., 1977, "Immunoreactivities of Polyclonal and Monoclonal Anti-T and Anti-Tn Antibodies with Human Carcinoma Cells, Grown In Vitro and in a Zenograft Model", *Int. J. Cancer*, 72:119-127.
S. Miotti et al., 1999 "Level of Anti-Mouse-Antibody Response Induced by Bi-Specific Monoclonal Antibody OC/TR in Ovarian-Carcinoma Patients is Associated with Longer Survival", *Int. J. CANCER*, 84-62-68.
J. A. Francisco et al., 1997, "In Vivo Efficacy and Toxicity of a Single-Chain Immunotoxin Targeted to CD40", *Blood*, 89:4493-4500.
C.F.M. Molthoff et al., 1997, "Escalating Protein Doses of Chimeric Monoclonal Antibody Mov18 Immunoglobulin G. In Ovarian Carcinoma Patients: A Phase I Study", *CANCER Supplement*, 80:2712-2720.
E. Kievit et al., 1997, "Determination of Tumor-Related Factors of Influence on the Uptake of the Monoclonal Antibody 323/A3 in Experimental Human Ovarian Cancer", *Int. J. Cancer*, 71:237-245.
K.O. Lloyd et al., 1997, "Isolation and Characterization of Ovarian Cancer Antigen CA 125 using a New Monoclonal Antibody (VK-8): Identification as a Mucin-Type Molecule", *Int. J. Cancer*, 71:842-580.
A. van Dalen, 1999, "BR-MA, OM-MA, GI-MA and CEA: Clinical Evaluation Using the IMMULITE Analyzer", *Tumore Biology*, 20:117-129.
G. Gebauer et al., 1999, "IMMULITE® OM-MA Assay: A Useful Diagnostic Tool in Patients with Benign and Malignant Ovarian Tumors", *Anticancer Research*, 19:2535-2536.

(Continued)

Primary Examiner—Stephen L Rawlings
(74) Attorney, Agent, or Firm—Locke Lord Bissell & Liddell, LLP

(57) ABSTRACT

The present invention is directed to cell surface antigens found on myeloma cells and on ovarian cancer cells that are recognized by monoclonal antibodies, and antibody binding fragments thereof, as described. The monoclonal antibodies of the invention are capable of being used for therapeutic, screening, diagnostic and cell purification purposes. A representative and exemplified monoclonal antibody of the present invention recognizes and binds to an epitope common to a surface antigen that is expressed on multiple myeloma cells and to a surface antigen that is expressed on ovarian cancer cells. The function of this monoclonal antibody both in vivo and in vitro is demonstrated.

22 Claims, 10 Drawing Sheets

OTHER PUBLICATIONS

S.P. Treon et al., 1999, "Muc-1 Core Protein Is Expressed on Multiple Myeloma Cells and Is Induced by Dexamethasone", *Blood*, 93:1287-1298.

K. Ono et al., 1999, "The humanized anti-HM1.24 antibody effectively kills multiple myeolma cells by human effector cell-mediated cytotoxicity", *Mol. Immunology*, 36:387-395.

G. Teoh et al., 1998, "The 86kD Subunit of Ku Autoantigen Mediates Homotypic and Heterotypic Adhesion of Multiple Myeloma Cells", *J. Clin. Invest.*, 101:1379-1388.

W.C.A.M. Buijs et al., 1998, "Dosimetric analysis of chimeric monoclonal antibody cMOv18 IgG in ovarian carcinoma patients after intraperitoneal and intravenouse administration", *Eur. J. Nuclear Medicine*, 25:1552-1561.

M.A. Bookman, 1998, Biological Therapy of Ovarian Cancer: Current Directions:, *Seminars in Oncology*, 25:381-396.

M. Kawata et al., 1998, "Detection of Epithelial Ovarian-Cancer-Associated Antigens Involved in Immune Complexes by Monoclonal Antibodies", *Tumor Biology*, 19:1-11.

S.A. McQuarrie et al., 1997, "Pharmacokinetics and radiation dosimetry of $^{99}Tc^m$-labelled monoclonal antibody B43.13 in ovarian cancer patients", *Nuclear Medicine Communications*, 18:878-886.

E. Kievit et al., 1997, "Comparison of the Biodistribution and the Efficacy of Monoclonal Antibody 323/A3 Labeled with Either $^{131}I$ or $^{186}Re$ in Human Ovarian Cancer Xenografts", *Int. J. Radiation Oncology bio. Phys.*, 38:813-832.

M. Hartman et al., 1999, "MUCI Isoform Specific Monoclonal Antibody 6E6/2 Detects Preferential Expression of the Novel MUC1/Y Protein in Breast and Ovarian Cancer", *Int. J. Cancer*, 82-256-267.

M.L. Grossbard et al., 1998 "Anti-B4-blocked ricin: a phase II trial of 7 day continuous infusion in patients with multiple myeloma", *British Journal of Haematology*, 102:509-515.

H. Bertz et al., 1997, "Adoptive immunotherapy for relapsed multiple myeloma after allogeneic bone marrow transplantation (BMT): evidence for a graft-versus-myeloma effect", *Leukemia*, 11:281-283.

J.L. Hornick et al., 1997, "Chimeric CLL-1 antibody Fusion Proteins Containing Granulocyte-Macrophage Colony-Stimulating Factor or Interleukin-2 with Specificity for B-Cell Malignancies Exhibit Enhanced Effector functions while Retaining Tumor Targeting Properties", *Blood*, 89:4437-4447.

D.G. Maloney et al., 1999, "Antibody Therapy for treatment of Multiple Myeloma", *Seminars in Hematology (Suppl.)*. 36:30-33.

V. Nuessler et al., 1997, "Functional P-gp expression in multiple myeloma patients at primary diagnosis and relapse or progressive disease" *Leukemia (Suppl.)*, 11:S10-S14.

G.J. Ossenkoppele, 1997, "Treatment of Multiple Myeloma in Elderly Patients", *Drugs & Aging*, 11:152-164.

T.H. Totterman et al., 1998, "Targeted Superantigens for Immunotherapy of Haematopoietic Tumors", *Vox Sanguinis*, 74:483-487.

M.G. Rosenblum et al., 1999, "Phase I Study of $^{90}Y$-labeled B72.3 Intraperitoneal Administration in Patients with Ovarian Cancer: Effect of Dose and EDTA Coadministration on Pharmacokinetics and Toxicity", *Clinical Cancer Research*, 5:953-961.

R.H. M. Verheijen et al., 1999, "CA 125: fundamental and clinical aspects", *Seminars in Cancer Biology*, 9:117-124.

G. Fleckenstein et al., 1998, "Monoclonal antibodies in solid tumours: approaches to therapy with emphasis on gynaecological cancer", *Medical Oncology*, 15:212-221.

E. Kievit et al., 1998 "[$^{186}Re$]-Labeled Mouse and Chimeric Monoclonal Antibody 323/A3: a Comparison of the Efficacy in Experimental Human Ovarian Cancer", *Nuclear Medicine & Biology*, 25:37-45.

S. Nicholson et al., 1998, "Radioimmunotherapy after chemotherapy compared to chemotherapy alone in the treatment of advanced ovarian cancer: A matched analysis", *Oncology Reports*, 5:223-226.

B.C. Schultes et al., 1998, Anti-idiotype induction therapy: anti-CA125 antibodies ($Ab_3$) mediated tumor killing in patients treated with Ovarex mAb B43.13 ($Ab_1$), *Cancer Immunol. Immunother*, 46:201-212.

M. Jojovic et al., 1998, "Epithelial glycoprotein-2 expression is subject to regulatory processes in epithelial-mesenchymal transitions during metastases: an investigation of human cancers transplanted into severe combined immunodeficient mice", *Histochemical Journal*, 30:723-729.

C. Kosmas et al., 1998, "Monoclonal Antibody Targeting of Ovarian Carcinoma", *Oncology*, 55:435-446.

M.F. Federici et al., 1999, "Selection of Carbohydrate Antigens in Human Epithelial Ovarian Cancers as Targets for Immunotherapy: Serous and Mucinous Tumors Exhibit Distinctive Patterns of Expression", *Int. J. Cancer*, 81:193-198.

W.G. McCluggage et al., 1998, "Immunocytochemical staining of ovarian cyst aspirates with monoclonal antibody against inhibin", *Cytopathology*, 9:336-342.

H.C.T. Van Zaanen et al., 1998, "Blocking Interleukin-6 Activity with Chimeric Anti-IL6 Monoclonal Antibodies in Multiple Myeloma: Effects on Soluble IL6 Receptor and Soluble gp 130", *Leukemia and Lymphoma*, 31:551-558.

V.L. Reichardt et al., 1997, "Rationale for adjuvant idiotypic vaccination after high-dose therapy for multiple myeloma", *Biol. Blood and Marrow Transplant*, 3:157-163.

N.L. Smith et al., 1999, "Immunohistochemically detecting target antigens in patient biopsies for tailoring monoclonal antibody based cancer therapy", *human Antibodies*, 9:61-65.

E. Harlow et al., 1988, "Labeling Antibodies", *Antibodies: A Laboratory Manual*, pp. 321-631.

N.S. Greenspan et al., 1999, "Defining epitopes: It's not as easy as it seems", *Nature Biotechnology*, 17:936-937.

P. Knight, 1989, "The Carbohydrate Frontier", *Biotechnology*, 7:35-40.

J.M. Cruse et al., 1995, *Illustrated Dictionary of Immunology*, p. 22.

W. Paul, 1993, *Fundamental Immunology*, Raven Press, NY Chpt 8, p. 242.

Partington K.M. et al.: "A Novel Method Of Cell Separation Based On Dual Parameter Immunomagnetic Cell Selection" *Journal of Immunological Methods*, vol. 223, No. 2; Mar. 4, 1999 pp. 195-205.

Tai Y -T et al.: "Isolation And Characterization Of Human Multiple Myeloma Cell Enriched Populations" *Journal of Immunological Methods*, vol. 235, No. 1-2; Feb. 2000; pp. 11-19.

Ozaki S. et al.: "Immunotherapy Of Multiple Myeloma With A Monoclonal Antibody Directed Against A Plasma Cell-Specific Antigen, HM1.24" *Blood*, W.B. Saunders, Philadelphia, VA, US; vol. 90, No. 8; Oct. 15, 1997.

\* cited by examiner

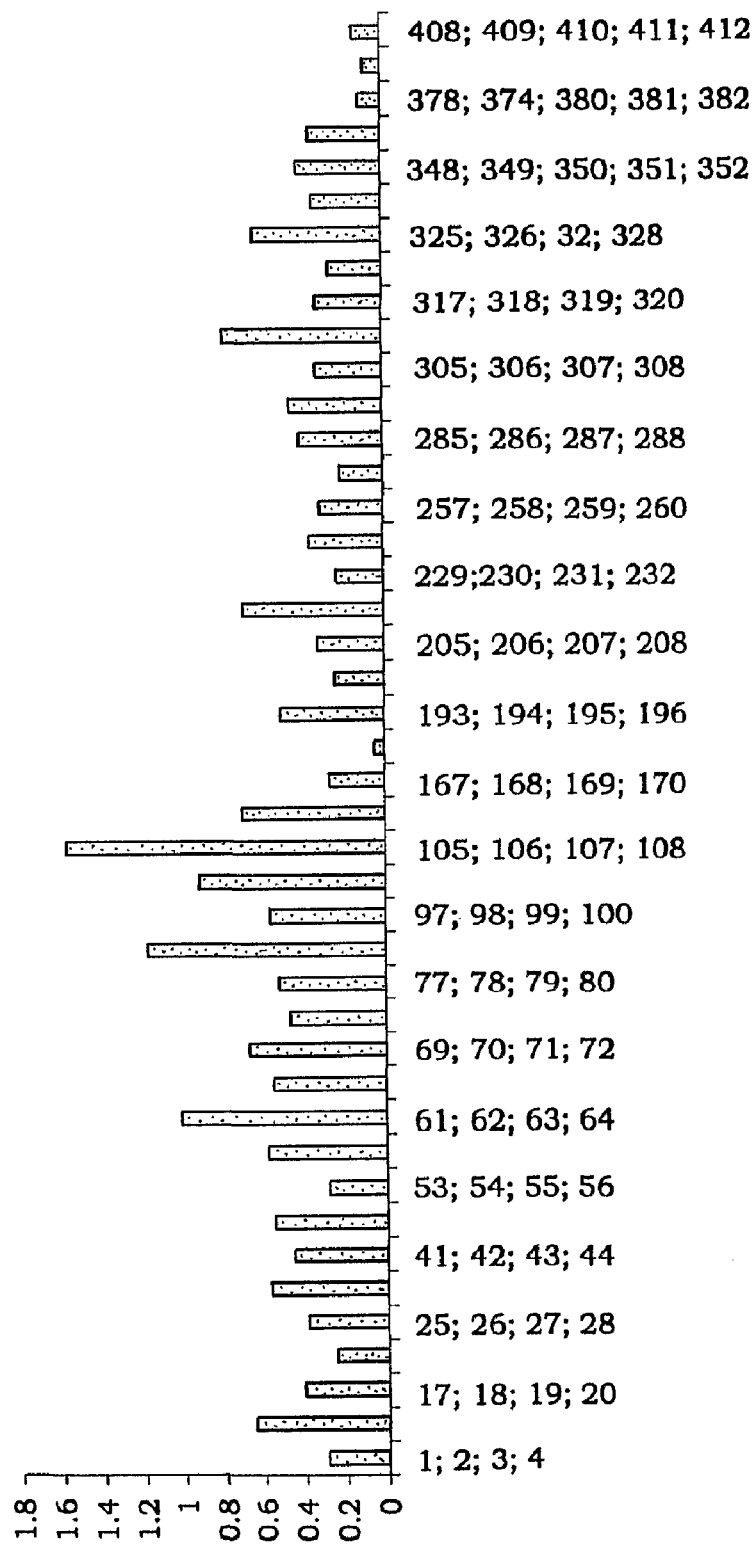

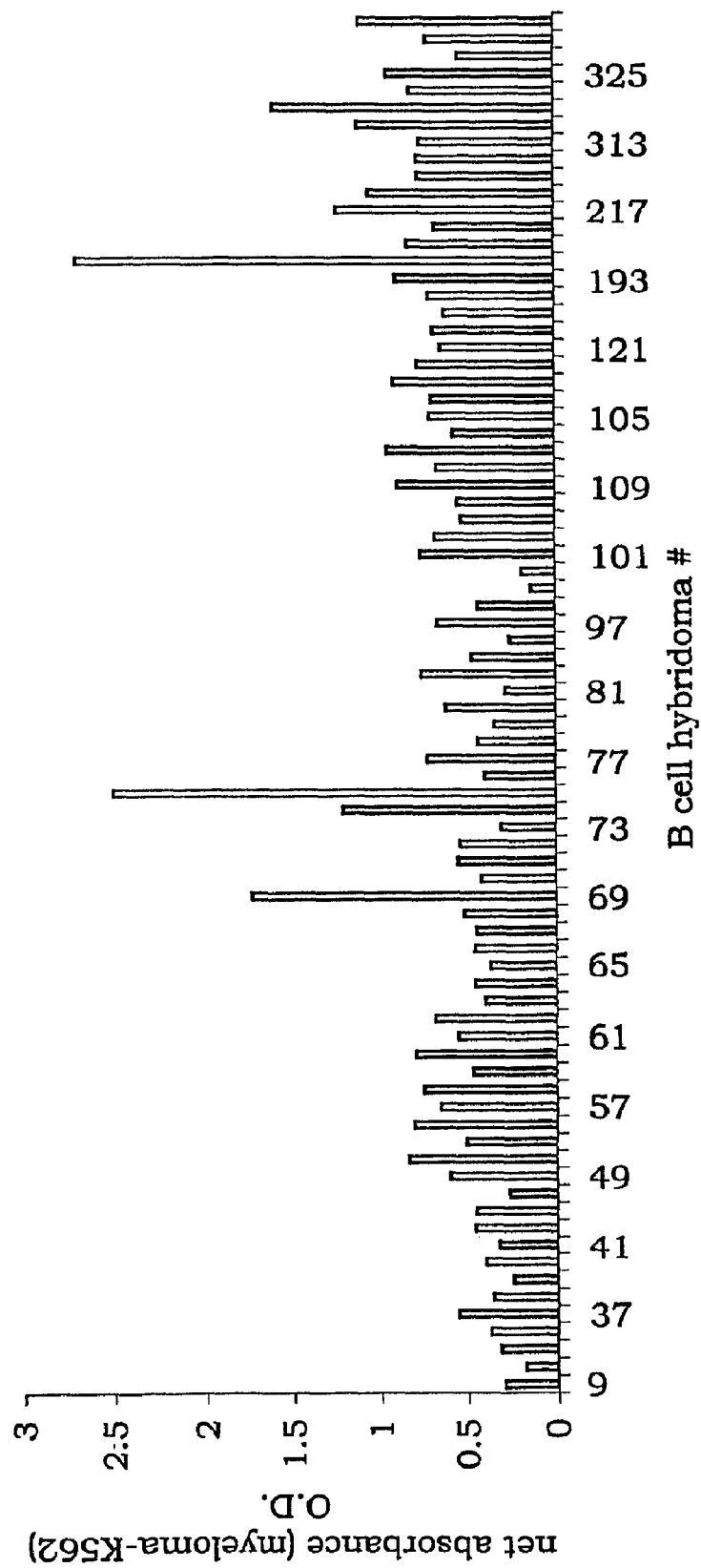

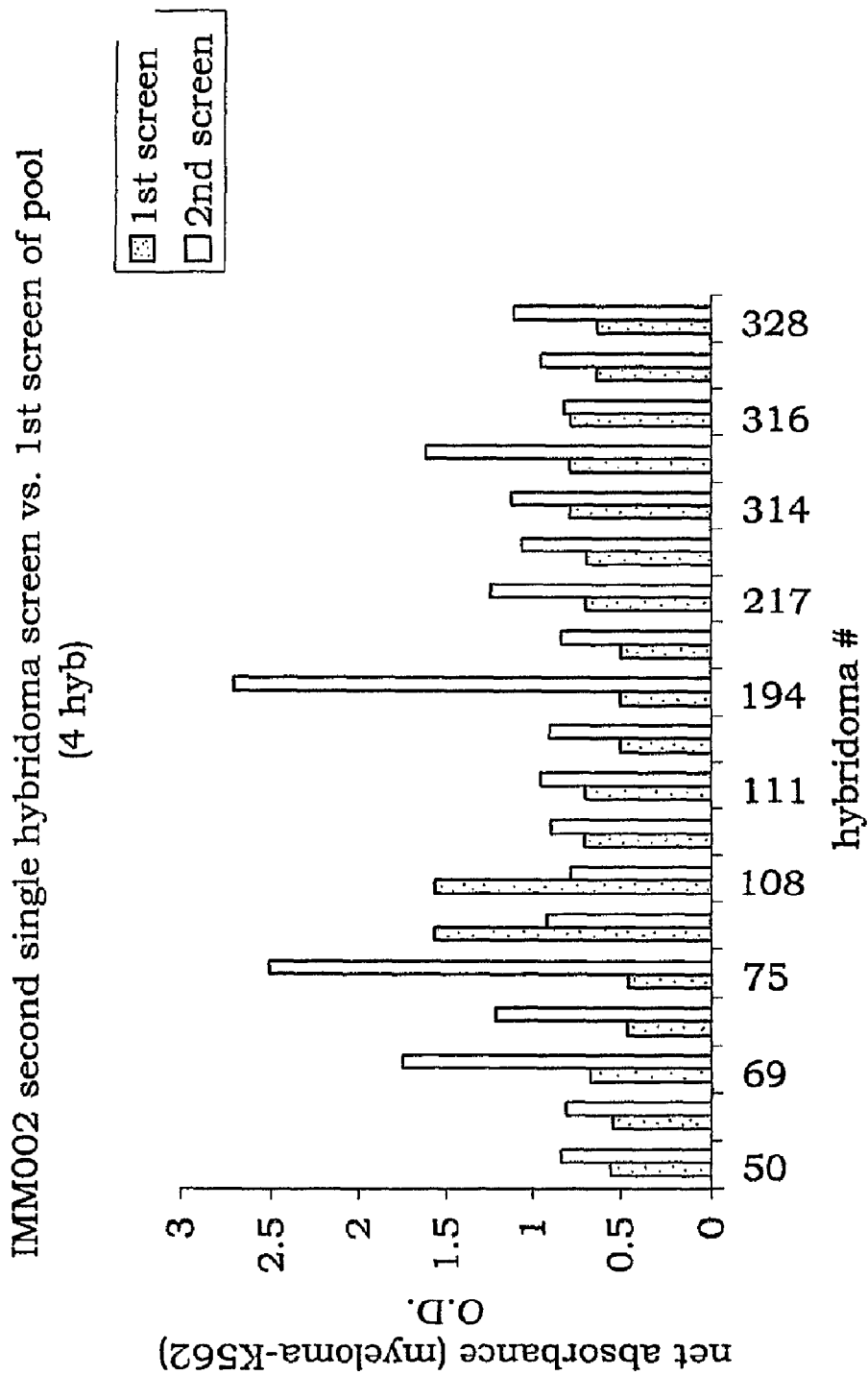

Generation of Moab specific to Multiple Myeloma:
*specificity assessment by FACS*

Moab (69)-specific antigen is shed by MM cells into the culture medium

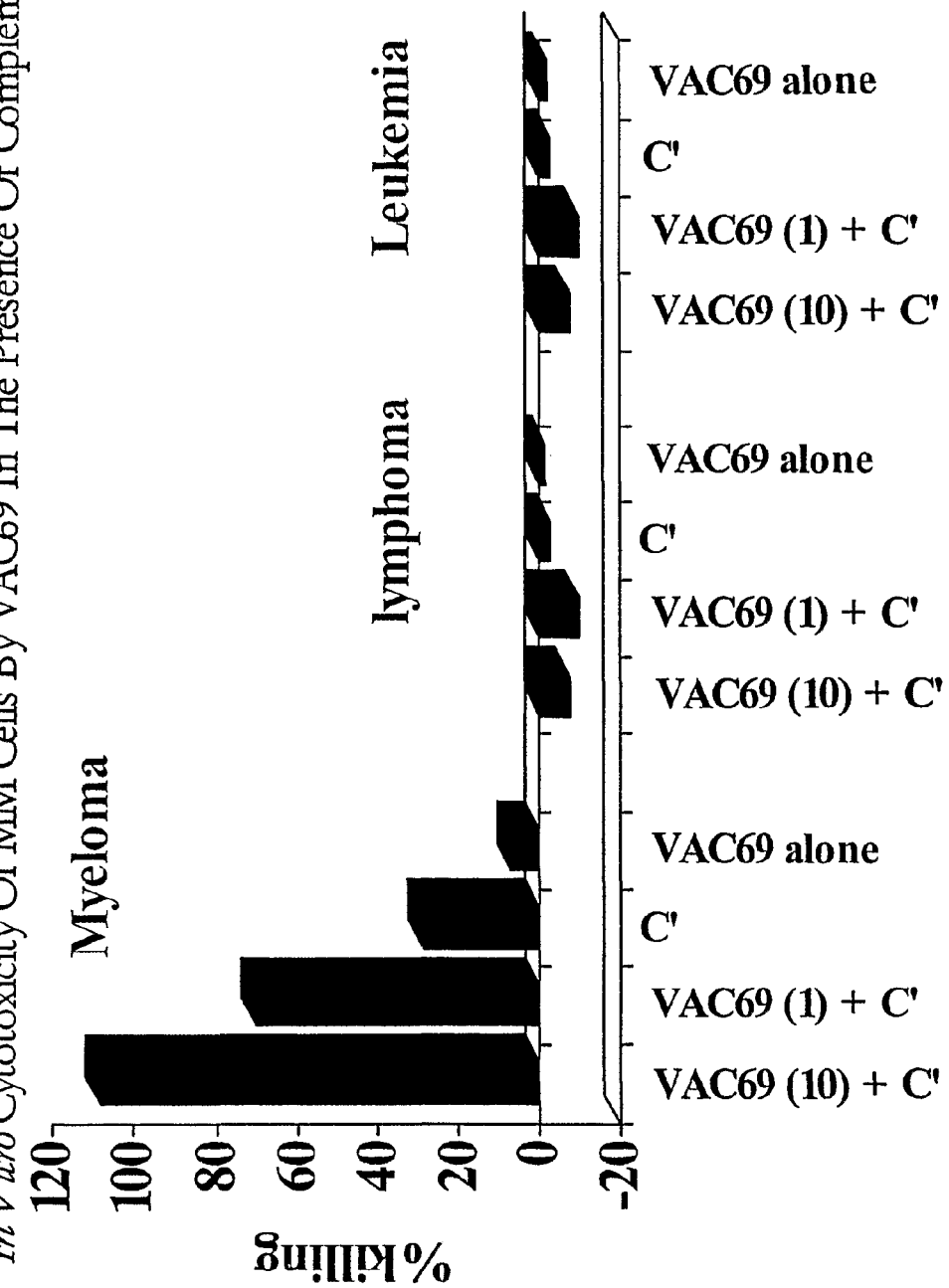

OVARIAN CANCER CELL AND MYELOMA CELL SURFACE GLYCOPROTEINS, ANTIBODIES THERETO, AND USES THEREOF

CROSS-REFERENCE TO RELATED APPLICATIONS

This application is a Divisional Application of U.S. patent application Ser. No. 10/049,608, filed Sep. 16, 2002, now U.S. Pat. No. 7,22,750 which is the national phase application under 35 U.S.C. §371 of the International Application Serial No. PCT/US2000/21574, filed Aug. 8, 2000, which is a continuation-in-part application of U.S. application Ser. No. 09/374,367, filed Aug. 13, 1999, now U.S. Pat. No. 6,376,654 all of which are incorporated herein by reference as if fully set forth herein.

FIELD OF THE INVENTION

The application is related to new surface glycoproteins of human myeloma cells and human ovarian tumor cells, monoclonal antibodies thereto, and methods of diagnosis and treatment of myeloma and ovarian cancer based thereon.

BACKGROUND OF THE INVENTION

Multiple myeloma (MM) embodies a plasma cell disorder characterized by neoplastic proliferation of a single clone of plasma cells engaged in the production of a monoclonal immunoglobulin, usually monoclonal IgG or IgA. MM accounts for 1% of all malignant disease and slightly more than 10% of all hematologic malignancies. The annual incidence of multiple myeloma is 4 per 100,000. The annual incidence is linked to aging population. The median age of patients at the time of diagnosis is 61 years. MM is most common in men, and in individuals of African ancestry.

MM remains a disease for which a cure is a rarity. Most patients succumb to their disease within 36-48 months from the time of diagnosis. The limitations of effective therapy for MM are primarily associated with a low cell proliferation rate and multi-drug resistance. Therapy for multiple myeloma includes induction, maintenance, and supportive aspects. The induction portion of the treatment aims at reducing the tumor volume and achieving a plateau phase. Different drugs and treatment modalities, such as bone marrow transplantation, have been entertained, and used without a significant impact on the disease or the overall survival.

Supportive care in multiple myeloma has advanced significantly over the past few years. Growth factor support with erythropoietin replacement and GM-CSF for stimulating the white blood cell (WBC) population are safe and effective methods of decreasing or preventing the occurrence or the severity of neutropenia. Also, high dose chemotherapy followed by autologous bone marrow or peripheral blood progenitor cell (PBMC) transplantation has recently increased the complete remission rate and remission duration. However, overall survival has only been slightly prolonged, and no evidence for a cure has been obtained. All patients ultimately relapse, even under maintenance therapy with interferon-α (IFN-α) alone or in combination with steroids. Adoptive immunotherapy rather than active vaccination may prove to be a more effective therapy for MM patients. There are relatively few known surface antigens on plasma cells that are suitable for antibody-directed treatment. Possible molecules include HM1.24, CD38, ICAM-1 (CD54), CD40, CD45, CD20, and syndecan 1. To date, there are no exclusive markers reported for MM. CD20, CD38, CD56 and CD130 are all markers that are expressed on normal B-cells, T-cells, or natural killer (NK) cells.

Ovarian cancer is the fifth leading cause of cancer deaths among U.S. women and has the highest mortality of any of the gynecologic cancers. It accounted for an estimated 26,600 new cases and 14,500 deaths in 1995. The overall 5-year survival rate is at least 75%, if the cancer is confined to the ovaries, and decreases to 17% in women diagnosed with distant metastases. Symptoms usually do not become apparent until the tumor compresses or invades adjacent structures, or ascites develops, or metastases become clinically evident. As a result, two thirds of women with ovarian cancer have advanced (Stage III or IV) disease at the time of diagnosis. Carcinoma of the ovary is most common in women over age 60. Other important risk factors include low parity and a family history of ovarian cancer. Less than 0.1% of women are affected by hereditary ovarian cancer syndrome, but these women may face a 40% lifetime risk of developing ovarian cancer.

Potential screening tests for ovarian cancer include the bimanual pelvic examination, the Papanicolaou (Pap) smear, tumor markers, and ultrasound imaging. The pelvic examination, which can detect a variety of gynecologic disorders, is of unknown sensitivity in detecting ovarian cancer. Although pelvic examinations can occasionally detect ovarian cancer, small, early-stage ovarian tumors are often not detected by palpation due to the deep anatomic location of the ovary. Thus, ovarian cancers detected by pelvic examination are generally advanced and associated with poor survival. The pelvic examination may also produce false positives when benign adnexal masses (e.g., functional cysts) are found. The Pap smear may occasionally reveal malignant ovarian cells, but it is not considered to be a valid screening test for ovarian carcinoma. Ultrasound imaging has also been evaluated as a screening test for ovarian cancer, since it is able to estimate ovarian size, detect masses as small as 1 cm, and distinguish solid lesions from cysts.

Serum tumor markers are often elevated in women with ovarian cancer. Examples of these markers include carcinoembryonic antigen, ovarian cystadenocarcinoma antigen, lipid-associated sialic acid, NB/70K, TAG 72.3, CA15-3, and CA-125, respectively. Evidence is limited on whether tumor markers become elevated early enough in the natural history of occult ovarian cancer to provide adequate sensitivity for screening. Tumor markers may have limited specificity. It has been reported that CA-125 is elevated in 1% of healthy women, 6-40% of women with benign masses (e.g., uterine fibroids, endometriosis, pancreatic pseudocyst, pulmonary hamartoma) and 29% of women with nongynecologic cancers (e.g., pancreas, stomach, colon, breast). Prospective studies involving asymptomatic women are needed, however, to provide definitive data on the performance characteristics of serum tests when used as screening tests.

SUMMARY OF THE INVENTION

In its broadest aspect, the present invention is directed to a monoclonal antibody, or binding fragment thereof, which specifically binds to antigens sharing a common epitope present on the surface of human myeloma cells and ovarian cancer cells. The antigen on multiple myeloma cells is a single glycosylated polypeptide with a molecular weight of about 78 kDa to about 120 kDa, as determined by SDS-PAGE under reducing conditions. The antigen on ovarian cancer cells is a single glycosylated polypeptide with a molecular weight of about 76 kDa to about 213 kDa, as determined by SDS-PAGE under reducing conditions. The antigens are absent from human peripheral blood mononuclear cells, absent from human B cells, and absent from human chronic myelongenic leukemia cells. Further, the antigens are not present on cells from a breast cancer tumor, not present on a prostate cancer cell line, not present on a neuroblastoma cell line, and not present on a cervical cancer cell line. The antigens are also not found on an Epstein-Barr virus-transformed B cell tumor.

A non-limiting example of the monoclonal antibody is that produced by the hybridoma cell line deposited at the American Type Culture Collection (ATCC®), 10801 University Boulevard, Manassas, Va. 20110-2209 on Aug. 3, 1999, and having ATCC Accession No. PTA-450. The monoclonal antibody produced by the deposited hybridoma cell line having ATCC Accession No. PTA-450 is termed both MoAb 69 and VAC69 herein.

The present invention is further directed to antibodies that are capable of binding to the same antigenic determinant as does the monoclonal antibody produced by the hybridoma cell line deposited at the American Type Culture Collection having ATCC Accession No. PTA-450; binding fragments of the hybridoma cell line deposited at the American Type Culture Collection having ATCC Accession No. PTA-450; and to binding fragments of a monoclonal antibody capable of binding to the same antigenic determinant as does the monoclonal antibody produced by the hybridoma cell line deposited at the American Type Culture Collection having ATCC Accession No. PTA-450.

Such monoclonal antibodies, or antibody fragments, may be human, or they may be derived from other mammalian species, such as rodent, hybrids thereof, chimeric antibodies, and the like. Binding fragments of the monoclonal antibodies of the present invention include, but are not limited to, F(ab')$_2$, Fab', Fv, Fd', or Fd fragments.

In another aspect, the present invention is directed to a cell line produced by a hybridoma technique, which produces a monoclonal antibody which specifically binds to surface antigens of human myeloma cells and of ovarian cancer cells. The antigen on multiple myeloma cells is a single glycosylated polypeptide with a molecular weight of about 78 kDa to about 120 kDa as determined by SDS PAGE under reducing conditions. The antigen on ovarian cancer cells is a single glycosylated polypeptide with a molecular weight of about 76 kDa to about 213 kDa, as determined by SDS-PAGE under reducing conditions. The antigens are absent from human peripheral blood mononuclear cells, absent from human B cells, and absent from human chronic myelongenic leukemia cells. A non-limiting example of a monoclonal antibody according to the present invention is that produced by the hybridoma cell line deposited at the American Type Culture Collection having accession No. PTA-450. Furthermore, the antigens are not present on cells from a breast cancer tumor, not present on a prostate cancer cell line, not present on a neuroblastoma cell line, and not present on a cervical cancer cell line. The antigens are also not found on an Epstein-Barr virus-transformed B cell tumor.

A further aspect of the present invention is the hybridoma cell line deposited at the American Type Culture Collection (ATCC®), 10801 University Boulevard, Manassas, Va. 20110-2209 on Aug. 3, 1999, and having ATCC Accession No. PTA-450.

Hybridoma cell line producing monoclonal antibody IMM002.69.47.4 has been deposited with the American Type Culture Collection (ATCC, P.O. Box 1549, Manassas, Va. 20108) on Aug. 3, 1999 under the provisions of the Budapest Treaty on the International Recognition of the Deposit of Microorganisms for the Purposes of Patent Procedures, and assigned accession numbers PTA-450, and incorporated herein by reference.

In another broad aspect of the present invention, an isolated surface antigen of human multiple myeloma cells is described, the antigen being a single glycosylated polypeptide with a molecular weight of about 78 kDa to about 120 kDa, as determined by SDS-PAGE under reducing conditions; the antigen being absent from human peripheral blood mononuclear cells, absent from human B cells, and absent from human acute myelogenic leukemia cells. The antigen is not present on cells from a breast cancer tumor, not present on a prostate cancer cell line, not present on a neuroblastoma cell line, and not present on a cervical cancer cell line. It is also not found on an Epstein-Barr virus-transformed B cell tumor. The isolated multiple myeloma surface antigen binds to a monoclonal antibody produced by the hybridoma cell line deposited at the American Type Culture Collection having ATCC Accession No. PTA-450.

In another broad aspect of the present invention, an isolated surface antigen of human ovarian cancer cells is described, the antigen being a single glycosylated polypeptide with a molecular weight of about 76 kDa to about 213 kDa, as determined by SDS-PAGE under reducing conditions; the antigen being absent from human peripheral blood mononuclear cells, absent from human B cells, and absent from human acute myelogenic leukemia cells. The antigen is not present on cells from a breast cancer tumor, not present on a prostate cancer cell line, not present on a neuroblastoma cell line, and not present on a cervical cancer cell line. It is also not found on an Epstein-Barr virus-transformed B cell tumor. The isolated ovarian cancer surface antigen binds to a monoclonal antibody produced by the hybridoma cell line deposited at the American Type Culture Collection having ATCC Accession No. PTA-450.

The present invention is also directed to methods of inhibiting the growth of, or killing, myeloma cells in a patient by administering the monoclonal antibody, or a binding fragment as described above, under conditions sufficient for the binding of the monoclonal antibody, or the binding fragment, to the myeloma cells to cause inhibiting or killing of the cancer cells by the immune cells of the patient. In another aspect, a method for inhibiting or killing myeloma cells in a patient is provided by administering the monoclonal antibody, or binding fragment as described above, which is conjugated with a cytotoxic moiety, under conditions sufficient for the binding of the monoclonal antibody, or binding fragment, to the cancer cells to inhibit the growth of, or to kill, the cells. The cytotoxic moiety may be, by way of non-limiting example, a chemotherapeutic agent, a photo-activated toxin, or a radioactive agent.

In still another aspect of the invention, the above-mentioned conjugate of the monoclonal antibody, or binding fragment, described herein and a cytotoxic moiety may be used in vitro to inhibit growth of, or kill, myeloma cells in a cellular sample, such as a bone marrow sample.

The invention is also directed to anti-idiotypic antibodies which mirror the binding site of the monoclonal antibody of the invention, and are specific to the myeloma and ovarian cancer conformational epitope recognized by the antibody of the invention. The invention is further directed to the use of the aforementioned anti-idiotypic antibodies for the treatment of MM or ovarian cancer by active immunization.

In a further aspect of the invention, a method is provided for removing myeloma cells from an isolated cellular sample, such as, but not limited to, bone marrow cells, by exposing the cellular sample to a solid matrix on which the monoclonal antibody, or binding fragment, described above is bound under conditions wherein the myeloma cells adhere to the monoclonal antibody, or binding fragment, and isolating a cellular fraction of said cellular sample which does not bind to the matrix. This method may be used, for example, in the removal of myeloma cells from a bone marrow sample for autologous bone marrow transplant.

The invention is also directed to the monoclonal antibody, or binding fragment, as described above bound to a solid support.

In yet another aspect of the invention, a method is provided for localizing myeloma cells or tumor cells, or ovarian cancer cells or tumor cells, in a patient by administering the monoclonal antibody, or binding fragment, as described above, allowing the monoclonal antibody, or binding fragment thereof, to bind to the cancer cells within said patient, and determining the location of the monoclonal antibody, or binding fragment thereof, within the patient. In another related aspect, the monoclonal antibody, or binding fragment, is detectably labeled, for example, with a radionuclide.

The present invention is further directed to methods of inhibiting the growth of, or killing, ovarian cancer cells in a patient by administering the monoclonal antibody, or binding fragment, as described above under conditions sufficient for the binding of the monoclonal antibody, or binding fragment, to the ovarian cancer cells to cause growth inhibition or killing of the ovarian cancer cells by immune cells of the patient. In another aspect, a method for inhibiting or killing ovarian cancer cells in a patient is provided by administering the monoclonal antibody, or binding fragment, as described above which is conjugated with a cytotoxic moiety, under conditions sufficient for the binding of the monoclonal antibody, or binding fragment, to ovarian cancer cells to cause growth inhibition or killing of the ovarian cancer cells. The cytotoxic moiety may be, by way of non-limiting example, a chemotherapeutic agent, a photo-activated toxin, or a radioactive agent.

In yet another aspect of the invention, a method is provided for localizing ovarian cancer cells in a patient by administering the monoclonal antibody, or binding fragment, described above, allowing the monoclonal antibody, or binding fragment thereof, to bind to ovarian cancer cells within said patient, and determining the location of said monoclonal antibody, or binding fragment thereof, within said patient. In another related aspect, the monoclonal antibody, or binding fragment, is detectably labeled, for example, with a radionuclide.

It is a further aspect of the invention to permit the detection of the cell surface glycoproteins described herein in a sample of bodily fluid, to aid in the diagnosis of multiple myeloma, ovarian cancer, or other cancer cells expressing a glycoprotein with the epitope recognized by the antibodies herein, by the detection of the glycoprotein antigen shed from cancer cells into the bodily fluid, such as blood. Furthermore, the stage of the disease may be monitored and the effectiveness of anti-cancer therapies can be monitored by determining the level or changes over time of the level of shed surface glycoprotein in a bodily fluid such as blood.

In still yet another aspect, the invention is directed to pharmaceutical compositions comprising a monoclonal antibody, or binding fragment, as described above and a pharmaceutically-acceptable carrier, diluent, or excipient.

In another aspect, the present invention is directed to a monoclonal antibody, or binding fragment, as described above labeled with a detectable moiety, such as, by way of non-limiting examples, a fluorophore, a chromophore, a radionuclide, or an enzyme.

These and other aspects of the present invention will be better appreciated by reference to the following drawings and Detailed Description.

BRIEF DESCRIPTION OF THE DRAWINGS

FIG. 1 depicts a first screen of B cell hybridomas generated from mice immunized with a pool of three human plasmacytoma cells compared with their binding to human myelogenic leukemia cell line (K562), which serves as a control.

FIG. 2 presents the results of selected hybridomas for the second screen.

FIG. 3 depicts the net binding values obtained for the first screen compared with the second screen.

FIG. 10 presents the results of an in vitro cytotoxicity assay performed using a human MM cell line (RPMI-8226), human lymphoma cell line (Namalwa) and chronic myelogenic leukemia cell line (K562). The tumor cells were incubated with VAC69 antibody at a concentration of 10 µg/ml or 1 µg/ml in the presence of human complement as described in Example 10. To assess the background level of cytotoxicity, the tumor cells were incubated with medium alone (untreated), complement alone, or with VAC69 alone. The cultures were pulsed with $^3$H-Thymidine and incubated for an additional 16 hours. The % killing of cancer cells was calculated from the values of $^3$H-Thymidine incorporation recorded for the test samples compared with the medium control (untreated).

DETAILED DESCRIPTION OF THE INVENTION

Figure 4A:
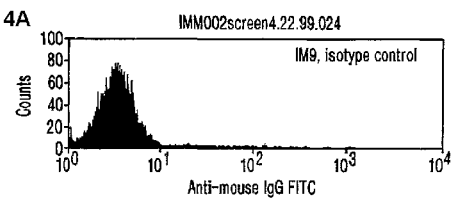
FIG. 4A-FIG. 4F present the results of cell surface staining using a panel of monoclonal antibodies and analyzed by flow cytometry.
Figure 4B:
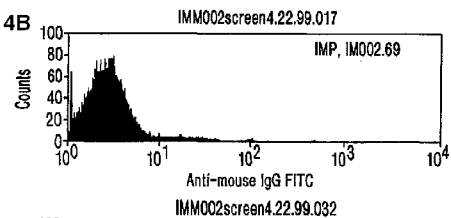
Figure 4C:
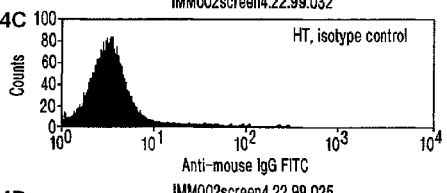
Figure 4D:
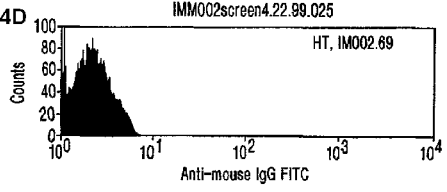
Figure 4E:
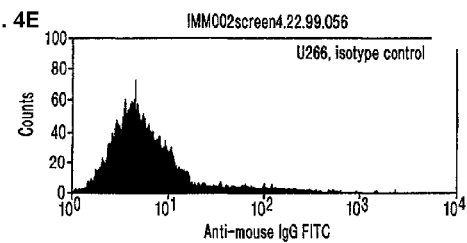
Figure 4F:
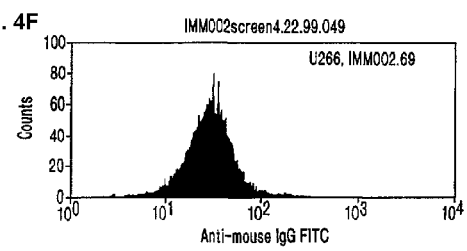

Identification of unique cancer antigens enables the design of selective immunotherapy for neoplastic diseases. The capacity to utilize a determinant exclusively expressed by cancer cells, and which is devoid in normal tissues, ensures the targeting and elimination of the neoplastic cells while insulating the function of normal cells. Although the last decades have witnessed great activity and significant success in the search for novel cancer antigens for various neoplastic diseases, cancer-specific antigens have not yet been defined for many malignancies. The majority of cancer antigens are self-antigens that are derived from and expressed by normal counterpart cells. Frequently, the cancer antigen is identical to the normal antigen even though it is expressed at higher levels, or endowed with a negligible mutation insufficient for its distinction from the self-antigen. One of the escape mechanisms of malignant cells from the immune system is their similarity to their normal counterpart cells, thus resulting in low visibility of the malignant cells by the immune system.

New surface glycoprotein antigens that are present on human myeloma cells and human ovarian cancer tumor cells, but absent from normal cells and from leukemic cells, are provided by the present invention. Such antigens present a target for therapeutic intervention in myeloma and ovarian cancer, as well as for diagnostic and cell purification purposes. These antigens share at least one common epitope.

A technique known as contrasting or differential immunization was employed for obtaining monoclonal antibodies to the antigen and for the identification of the novel cancer antigens described herein. As described in the examples below, two divergent immunogens provided at different locations were used. The dual immunization polarizes the migration of the distinct populations of immune cells to discrete draining lymph nodes. In an example herein, a mixture of human myeloma cells was used as the immunogen to obtain murine monoclonal antibodies to a myeloma cell surface antigen. Control cells in this example, i.e., a related, myelogenic leukemic cell line, were used to polarize the immune response to effectively delete undesired cells from the lymph nodes near the site of immunization with the desired antigen. The immune cells extracted from the draining lymph nodes close to the immunization site with the desired neoplasms were immortalized by fusion with murine myeloma cells. The antipodal draining lymph nodes were populated with immune cells specific to the undesired (control) immunogens.

By use of the foregoing protocol, a series of monoclonal antibodies were prepared which were found to bind specifically to antigens on the surfaces of human myeloma cells and on ovarian cancer cells. These antigens share at least one epitope. The antigens are further characterized in that the antigen on multiple myeloma cells is a single glycosylated polypeptide with a molecular weight of about 78 kDa to about 120 kDa, as determined by SDS-PAGE under reducing conditions; and it is absent from human peripheral blood mononuclear cells, absent from human B cells, and absent from human B cell myelogenic leukemia cells.

The antigen on ovarian cancer cells is a single glycosylated polypeptide with a molecular weight of about 76 kDa to about 213 kDa, as determined by SDS-PAGE under reducing conditions; and it is absent from human peripheral blood mononuclear cells, absent from human B cells, and absent from human B cell myelogenic leukemia cells. An antigen recognized by the antibody of the invention is also present on liver cancer cells; thus, the liver cancer cell surface antigen has at least one epitope in common with the myeloma and ovarian cancer surface glycoprotein. An example of a hybridoma cell line that produces a monoclonal antibody which recognizes these antigens has been deposited at the American Type Culture Collection (ATCC®), 10801 University Boulevard, Manassas, Va. 20110-2209, on Aug. 3, 1999, and accorded ATCC Accession No. PTA-450.

The aforementioned antigens were found not to be present on cells from a breast cancer tumor, and were not present on a prostate cancer cell line, or on a neuroblastoma cell line, or on a cervical cancer cell line. They were also not found on an Epstein-Barr virus-transformed B cell tumor.

As further exemplified herein, VAC69, the monoclonal antibody produced by the hybridoma deposited under ATCC Accession No. PTA-450 was shown to react with a single chain cell surface glycoprotein with a $M_r$ of about 78 kDa to about 120 kDa. The VAC69 MoAb did not react with an array of human cancers such as lung, prostate, breast, cervical, neuroblastoma, lymphoma and leukemia. In addition, the antigen was not detected in human normal tissues such as those derived from breast, ovary, prostate, colon, or lung. Interestingly, VAC69, when tested on a panel of human malignancies reacted with ovarian cancer. VAC69-reactive antigen expressed by ovarian cancer cells appears to be distinct from that expressed by MM by its pattern of expression, i.e., being either a single high $M_r$ glycoprotein (~200 kDa) or a set of glycoproteins with a $M_r$ of about 76 kDa to about 213 kDa. One ovarian tumor expressed a single high $M_r$ band, thereby indicating that the existence of a multiple subunit antigen is unlikely. Accordingly, the lower $M_r$ bands may represent degradation products of the larger glycoprotein. The increase in $M_r$ of the glycoprotein expressed by ovarian cancer compared with that expressed by the MM antigen may imply that VAC69 recognizes a communal epitope on two distinct antigens.

The present invention is directed to monoclonal antibodies, and binding fragments thereof, which recognize the aforementioned myeloma cell and ovarian cancer cell surface glycoproteins. Thus, the present invention embraces the deposited monoclonal antibody described above and monoclonal antibodies and their binding fragments having binding specificity for the aforementioned antigens. Such antibody fragments capable of binding the aforementioned antigens, include, but are not limited to, F(ab')$_2$ fragments, Fab' fragments, Fv fragments, Fd' fragments, or Fd fragments. Antibodies may be human, mammalian, such as mouse, and hybrid or chimeric antibodies. The antibody fragments and means for preparing then from antibodies are known to one of skill in the art.

The monoclonal antibodies and antibody binding fragments may be characterized as those which are 1) produced from the hybridoma cell line deposited at the American Type Culture Collection and having ATCC Accession No. PTA-450; 2) capable of binding to the same antigenic determinant as does the monoclonal antibody produced by the hybridoma cell line deposited at the American Type Culture Collection having ATCC Accession No. PTA-450; 3) binding fragments of the hybridoma cell line deposited at the American Type Culture Collection having ATCC Accession No. PTA-450; or 4) binding fragments of a monoclonal antibody capable of binding to the same antigenic determinant as does the monoclonal antibody produced by the hybridoma cell line deposited at the American Type Culture Collection having ATCC Accession No. PTA-450.

Accordingly, the aforementioned monoclonal antibodies and binding fragments recognize a common epitope of cell surface glycoproteins present on human myeloma cells and on human ovarian cancer cells, but absent from human peripheral blood mononuclear cells, absent from human B cells, and absent from human B cell myelogenic leukemia cells. Further, the cell surface glycoprotein on myeloma cells is a single polypeptide with a molecular weight of about 78 kDa to about 120 kDa, as determined by SDS-PAGE under reducing conditions. The cell surface glycoprotein on ovarian cancer ells is a single polypeptide with a molecular weight of about 76 kDa to about 213 kDa, as determined by SDS-PAGE under reducing conditions. As the myeloma, ovarian cancer, and liver cancer cell surface glycoproteins share a common epitope recognized by the antibodies of the invention, such antibodies may be used therapeutically and diagnostically for these conditions. As mentioned above, the antigen is also present on the surface of liver cancer cells, but is not present on cells from a breast cancer tumor, not present on a prostate cancer cell line, not present on a neuroblastoma cells line, and not present on a cervical cancer cell line. It is also not found on an Epstein-Barr virus-transformed B cell tumor.

The present invention is also directed to hybridoma cell lines which produce a monoclonal antibody which specifically binds to the surface antigens of human myeloma cells and ovarian cancer cells as described and characterized herein. These antigens have a shared region or an epitope contained in the cell surface glycoproteins of these neoplasms. The methods for the preparation of such hybridomas are known to the skilled artisan. The contrasting immunization procedure described herein is but one example of various means for obtaining the desired antibodies. For preparation of monoclonal antibodies directed toward the surface glycoprotein antigens described herein, any technique that provides for the production of antibody molecules by continuous cell lines in culture may be used. For example, such techniques include, but are not limited to, the hybridoma technique originally developed by Kohler and Milstein (*Nature*, 256:495-497, 1975), as well as the trioma technique, the human B-cell hybridoma technique (Kozbor et al., *Immunology Today*, 4:72, 1983; Cote et al., *Proc. Natl. Acad. Sci. U.S.A.*, 80:2026-2030, 1983), and the EBV-hybridoma technique to produce human monoclonal antibodies (Cole et al., in *Monoclonal Antibodies and Cancer Therapy*, Alan R. Liss, Inc., pp. 770-96, 1985).

In another embodiment of the present invention, monoclonal antibodies can be produced in germ-free animals utilizing the technology described in international application number WO 98/02545. Also, according to the invention, techniques developed for the production of "chimeric antibodies" are suitable for use. Preferred are human or humanized chimeric antibodies for use in therapy of human diseases or disorders as described infra, since the human or humanized antibodies themselves are much less likely than xenogenic antibodies to induce an immune response, particularly an allergic response.

According to the present invention, techniques described for the production of single chain antibodies (U.S. Pat. Nos. 5,476,786 and 5,132,405 to Huston; and U.S. Pat. No. 4,946,778) can be adapted to produce myeloma surface antigen-specific single chain antibodies. An additional embodiment of the invention utilizes the techniques described for the construction of Fab expression libraries (Huse et al., *Science*, 246:1275-1281, 1989) to allow the rapid and easy identification of monoclonal Fab fragments with the desired specificity, or fragment derivatives, or analogs.

Antibody fragments which contain the idiotype of the antibody molecule can also be generated by known techniques. For example, such fragments include, but are not limited to, the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

As mentioned above, the present invention is also directed to the isolated surface antigens of human myeloma cells and human ovarian cancer cells, wherein the human myeloma cell-expressed antigen is characterized as being a single glycosylated polypeptide with a molecular weight of about 78 kDa to about 120 kDa, as determined by SDS-PAGE under reducing conditions and the human ovarian cancer cell-expressed antigen is characterized as having a molecular weight of about 76 kDa to about 213 kDa. These antigens are absent from human peripheral blood mononuclear cells, absent from human B cells, and absent from human B cell myelogenic leukemia cells. The antigens are also absent from breast cancer cells, as determined using fresh tumor tissue; absent from prostate cancer cells, determined using a prostate cancer cell line; absent from neuroblastoma cells, as determined using a neuroblastoma cell line, and absent from cervical cancer cells as determined by using a cervical cancer cell line. The glycoproteins have been found to be present on the surfaces of cells from a freshly-isolated liver cancer tumor. Thus, the above-described methods are also applicable to the therapy and diagnosis of liver cancer. The isolated surface antigens are further characterized in that they bind to the monoclonal antibody produced by the hybridoma cell line deposited at the American Type Culture Collection having ATCC Accession No. PTA-450.

The monoclonal antibody MA69 reacts consistently with a single chain glycoprotein with a molecular weight of 78-120 kDa on multiple myeloma (MM) cells. On ovarian carcinoma cells, however, MA69 recognizes one or more glycoproteins ranging in size from 76 to 213 kDa. These results imply that MA69 reacts with two distinct molecules expressed on MM and ovarian cancer cells through the recognition of a shared region or an epitope contained in the cell surface glycoproteins of these neoplasms. This epitope is uniquely expressed on cells of ovarian and MM malignancies and was not found on the cell surfaces of a panel of human tumors, such as lung cancer, cervical cancer, neuroblastoma, breast cancer, prostate cancer, leukemia and lymphomas. Thus, the present invention is also generally directed to cell surface glycoproteins which comprise an epitope recognized by the antibodies of the invention. As noted above, cell surface glycoproteins comprising this epitope are absent from the various normal and cancer cells tested and listed above.

The present invention is also directed to therapeutic methods for the treatment of myeloma and related dysproliferative diseases in humans, including multiple myeloma, as well as ovarian cancer, using the antibodies of the present invention. The therapeutic and diagnostic uses described herein embrace primary tumors as well as metastases. For example, a method for inhibiting or killing myeloma cells or ovarian cancer cells in a patient may be carried out by administering to the patient, in a single dose or in successive doses, the monoclonal antibody, or antibody binding fragment as described above, under conditions sufficient for the binding of the monoclonal antibody, or binding fragment, to tumor cells in the patient. Binding of antibodies to the tumor cells induces the growth inhibition and/or killing of the tumor cells by immune cells in the patient.

The aforementioned therapy may be accompanied by other treatments directed at the tumor cells, such as chemotherapy, radiation, etc., as well as by adjunctive therapies to enhance the immune system's attack on the opsonized tumor cells following the procedure described above. For example, a growth factor such as erythropoietin and/or GM-CSF can be co-administered to the patient for stimulating the white blood cells and supporting the immunocompetence status of the patient.

Further, chimeric or other recombinant antibodies of the invention may be used therapeutically. For example, a fusion protein comprising at least the antigen-binding region of the antibody of the invention joined to at least a functionally active portion of a second protein having anti-tumor effects, e.g., a lymphokine or oncostatin, may be used to treat a human tumor in vivo. In addition, a chimeric antibody, wherein the antigen-binding site is joined to human Fc region, e.g., IgG1, may be used to promote antibody-dependent mediated cytotoxicity or complement-mediated cytotoxicity. In addition, recombinant techniques known in the art can be used to construct bispecific antibodies wherein one of the binding specificities is that of the antibody of the invention (See, e.g., U.S. Pat. No. 4,474,893).

It will be appreciated by the skilled practitioner that other dysproliferative diseases in which the glycoprotein antigens of the invention are present on the cell surface are treatable by the methods described herein.

The above-described methods utilize the antibodies or binding fragments without modification, relying on the binding of the antibodies or fragments to the surface antigen(s) of the myeloma or ovarian cancer cells in situ to stimulate an immune attack thereon. In another aspect of the therapeutic methods, the aforementioned method may be carried out using the monoclonal antibodies or binding fragments to which a cytotoxic agent is bound. Binding of the cytotoxic antibodies, or antibody binding fragments, to the tumor cells inhibits the growth of or kills the cells. By way of non-limiting example, suitable cytotoxic agents may be a chemotherapeutic agent, a photo-activated toxin or radioactive agent. For example, cytotoxic agents such as ricin A chain, abrin A chain, modeccin A chain, gelonin, melphalan, bleomycin, adriamycin, daunomycin, or pokeweed antiviral proteins (PAP, PAPII, PAP-S).

Those skilled in the art will realize that there are numerous radioisotopes and chemocytotoxic agents that can be coupled to tumor specific antibodies by well known techniques, and delivered to specifically destroy tumor tissue. See, e.g., U.S. Pat. No. 4,542,225 to Blattler et al. Examples of photo-activated toxins include dihydropyridine- and omega-conotoxin (Schmidt et al., *J Biol. Chem.*, 1991, 266(27):18025-33). Examples of imaging and cytotoxic reagents that can be used include $^{125}$I, $^{111}$In, $^{123}$I, $^{99m}$Tc, $^{32}$P, $^{3}$H, and $^{14}$C; fluorescent labels such as fluorescein and rhodamine, and chemiluminescers such as luciferin. The antibody can be labeled with such reagents using techniques known in the art. For example, see Wenzel and Meares, *Radioimmunoimaging and Radioimmunotherapy*, Elsevier, New York (1983) for techniques relating to the radiolabeling of antibodies (see also, Colcer et al., "Use of Monoclonal Antibodies As Radiopharmaceuticals For The Localization Of Human Carcinoma Xenografts In Nude Mice", *Methods Enzymol.*, 121:802-16, 1986: "Order, Analysis, Results and Future Prospective of the Therapeutic Use of Radiolabeled Antibody in Cancer Therapy", in *Monoclonal Antibodies for Cancer Detection and Therapy*, Baldwin et al. (eds), pp. 303-16 (Academic Press 1985).

Other covalent and non-covalent modifications of the antibodies or antibody fragments of the present invention are embraced herein, including agents which are co-administered or administered after the antibody or fragments, to induce growth inhibition or killing of the cells to which the antibody or fragment has previously bound.

Anti-idiotypic monoclonal antibodies to the antibodies of the invention may also be used therapeutically in active tumor immunization and tumor therapy (see, e.g., Hellstrom et al., "Anti Idiotypes" in *Covalently Modified Antigens and Antibodies in Diagnosis and Therapy*, supra at pp. 35-41).

In the area of multiple myeloma, the antibodies or antibody fragments of the present invention have further utility in the preparation of cellular samples from which myeloma cells have been removed. This use is particularly important in autologous bone marrow transplants, wherein a sample of bone marrow is harvested from a cancer patient prior to the patient's undergoing high-dose chemotherapy. The goal of the high dose chemotherapy is to destroy the cancer cells, which also results in the depletion of bone marrow cells. Following such treatment, the harvested bone marrow cells are reintroduced into the patient.

In myeloma and related diseases, the harvested bone marrow is contaminated with myeloma cells; thus, reintroduction of untreated bone marrow will simply reintroduce the disease. Previous methods to prevent reintroduction of cancer cells have included treatment of the bone marrow sample with chemotherapeutic agents and other anti-neoplastic agents in vitro. Other methods include purging the sample of cancer cells.

In a further practice of the present invention, the monoclonal antibodies and fragments described herein may be used to remove myeloma cells from a patient's bone marrow sample before reintroduction into the patient. In one nonlimiting example, the monoclonal antibodies, or binding fragments, are attached to a matrix, such as beads. This may be accomplished by any of several well-known methods for preparing an affinity matrix comprising antibodies or their binding fragments. The bone marrow sample is then exposed to the matrix, such as by passage of the cells over a column containing the matrix, under conditions to promote the binding of the myeloma cells in the sample through antigen/antibody interactions with the antibodies or binding fragments attached to the matrix. The myeloma cells in the sample adhere to the matrix; while the column effluent, i.e., the non-adherent cellular population, is depleted of myeloma cells. The effectiveness of the procedure may be monitored by examining the cells for residual myeloma cells, such as by using a detectably-labeled antibody as described below. The procedure may be repeated or modified to increase effectiveness.

This purging procedure (see, e.g., Ramsay et al., *J. Clin. Immunol.*, 8(2):81-88, 1988) may be performed together with other methods for removing or killing cancer cells, including, but not limited to, exposing the purified bone marrow cells to chemotherapeutic agents. Such chemotherapeutic agents include the use of the antibodies or antibody binding fragments of the present invention conjugated to a cytotoxic agent, as those described above for in vivo therapeutic treatment. Accordingly, conjugates of the antibodies or antibody fragments of the present invention with cytotoxic agents may be used for the ex vivo killing of tumor cells in a cellular sample. The methods may additionally include exposing the cells to cytokines (e.g., GM-CSF, IL-6), cytokine receptors (e.g., IL-6-receptor), mitogens (e.g., poke weed mitogen (PWM)), or adhesion molecules (e.g., CD40 ligand) in order to stimulate the myeloma cells to rapidly differentiate and thereby upregulate expression of cancer-specific antigens on their cell surface. These treatment modalities are intended to render the myeloma cells vulnerable to the in vitro-mediated cytotoxicity achieved by incubation with the monoclonal antibody, or fragments thereof, according to the present invention.

In a related aspect of the present invention, the monoclonal antibodies according to this invention can be used for immunotherapy, either unlabeled or labeled with a therapeutic agent. These therapeutic agents can be coupled either directly or indirectly to the described monoclonal antibodies, using techniques routinely practiced in the art. One example of indirect coupling is by the use of a spacer moiety. Spacer moieties, in turn, can be either insoluble or soluble (Dieher et al., 1986, *Science*, 231:148) and can be selected to enable drug release from the monoclonal antibody molecule at the target site. Examples of therapeutic agents which can be coupled to the monoclonal antibodies of the invention for anti-cancer immunotherapy are drugs, radioisotopes, lectins, and toxins.

The drugs with which can be conjugated to the monoclonal antibodies of the present invention include non-proteinaceous as well as proteinaceous compounds. The term "non-proteinaceous drugs" encompasses compounds which are classically referred to as drugs, for example, mitomycin C, daunorubicin, and vinblastine. The proteinaceous drugs with which the monoclonal antibodies of the invention can be labeled include immunomodulators and other biological response modifiers.

The term "biological response modifiers" is meant to encompass substances that are involved in modifying the immune response in such manner as to enhance the destruction of the antigen-bearing tumor for which the monoclonal antibodies of the invention is specific. Examples of immune response modifiers include such compounds as lymphokines. Lymphokines include tumor necrosis factor, interleukins, e.g., IL1 through IL15, lymphotoxin, macrophage activating factor (MAF), migration inhibition factor (MIF), colony stimulating factor (CSF), and interferon. Interferons with which the monoclonal antibodies of the invention can be labeled include alpha-interferon, beta-interferon and gamma-interferon and their subtypes.

In using radioisotopically conjugated monoclonal antibodies of the invention for immunotherapy, certain isotopes may be more preferable than others depending on such factors as leukocyte distribution as well as isotope stability and emission. If desired, the tumor cell distribution can be evaluated by the in vivo diagnostic techniques described above. Depending on the malignancy, some emitters may be preferable to others. In general, alpha and beta particle-emitting radioisotopes are preferred in immunotherapy. For example, if an animal has solid tumor foci, as in a carcinoma, a high energy beta emitter capable of penetrating several millimeters of tissue, such as $^{90}$Y, may be preferable. On the other hand, if the malignancy consists of simple target cells, as in the case of leukemia, a shorter range, high energy alpha emitter, such as $^{212}$Bi, may be preferable. Examples of radioisotopes which can be bound to the monoclonal antibodies of the invention for therapeutic purposes are $^{251}$I, $^{131}$I, $^{90}$Y, $^{67}$Cu, $^{212}$Bi, $^{211}$At, $^{212}$Pb, $^{47}$Sc, $^{109}$Pd, and $^{188}$Re.

Lectins are proteins, usually isolated from plant material, which bind to specific sugar moieties. Many lectins are also able to agglutinate cells and stimulate lymphocytes. Ricin is a toxic lectin that has been used immunotherapeutically. This is preferably accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin (DT), a substance produced by *Corynebacterium diphtheria*, can be used therapeutically. DT consists of an alpha and beta subunit which under proper conditions can be separated. The toxic alpha component can be bound to an antibody and used for site specific delivery to a cell bearing an antigen for which the monoclonal antibodies of the invention are specific. Other therapeutic agents which can be coupled to the monoclonal antibodies of the invention are known, or can be easily ascertained, by those of ordinary skill in the art.

The labeled or unlabeled monoclonal antibodies of the present invention can also be used in combination with therapeutic agents such as those described above. Especially preferred are therapeutic combinations comprising the monoclonal antibody of the invention and immunomodulators and other biological response modifiers. Thus, for example, the monoclonal antibodies of the invention can be used in combination with alpha-interferon. This treatment modality enhances monoclonal antibody targeting of carcinomas by increasing the expression of monoclonal antibody reactive antigen by the carcinoma cells (Greiner et al., 1987, *Science*, 235:895). Alternatively, the monoclonal antibodies of this invention may be used, for example, in combination with gamma-interferon to activate and increase the expression of Fc receptors by effector cells, which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibodies of the invention.

When the monoclonal antibodies of the present invention are used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the tumor, the condition of the patient and the half-life of the agent.

Using the monoclonal antibodies of the present invention, it is possible to design therapies combining all of the characteristics described herein. In a given situation, it may be desirable to administer a therapeutic agent, or agents, prior to the administration of the monoclonal antibodies of the invention, in combination with effector cells and the same, or different, therapeutic agent or agents. For example, it may be desirable to treat patients with malignant disease by first administering gamma-interferon and interleukin-2 daily for 3 to 5 days, and on day 5 administer the monoclonal antibody of the invention in combination with effector cells, as well as gamma-interferon, and interleukin-2.

It is also possible to utilize liposomes with the monoclonal antibodies of the present invention in their membranes to specifically deliver the liposome to the area of the tumor expressing SCLC-specific antigens. These liposomes can be produced such that they contain, in addition to monoclonal antibody, immunotherapeutic agents, such as those described above, which would then be released at the tumor site (e.g., Wolff et al., 1984, *Biochem. et Biophys. Acta*, 802:259).

The dosage ranges for the administration of the monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of disease of the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days.

Generally, when the monoclonal antibodies of the present invention are administered conjugated with therapeutic agents, lower dosages, comparable to those used for in vivo immunodiagnostic imaging, can be used. The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

In another aspect of the therapeutic methods of the present invention, the antibodies, or binding fragments thereof, conjugated with cytotoxic agents, such as chemotherapeutic agents, a photo-activatable toxin, or a radionuclide, may be used in vitro or ex vivo to inhibit or kill myeloma cells from a bone marrow sample, in the absence of the purging technique described above. The treatment of a sample with the cytotoxic antibodies, or antibody fragments, may be combined with other methods to kill cancer cells to increase the effectiveness of a bone marrow transplant, particularly an autologous bone marrow transplant, by removing cells from the tissue to be transplanted. These methods may include additionally exposing the cells to cytokines, etc. Thus, a method is described herein for removing myeloma cells from a isolated cellular sample comprising the steps of exposing the cellular sample to a solid matrix on which a monoclonal antibody, or antibody binding fragment as described herein, is bound under conditions in which the myeloma cells adhere to the monoclonal antibody, or binding fragment thereof, and isolating a cellular fraction of the cellular sample which does not bind to the matrix. By way of non-limiting example, bone marrow cells are used, particularly for a transplant, and preferably, an autologous bone marrow transplant.

In a further aspect of the present invention, compositions are provided which comprise the monoclonal antibody, or antibody binding fragment as described herein, bound to a solid support. A solid support for use in the present invention will be inert to the reaction conditions for binding. A solid phase support for use in the present invention must have reactive groups or activated groups in order to attach the monoclonal antibody or its binding partner thereto. In another embodiment, the solid phase support may be a useful chromatographic support, such as the carbohydrate polymers SEPHAROSE®, SEPHADEX®, or agarose. As used herein, a solid phase support is not limited to a specific type of support. Rather, a large number of supports are available and are known to one of ordinary skill in the art. Solid phase supports include, for example, silica gels, resins, derivatized plastic films, glass beads, cotton, plastic beads, alumina gels, magnetic beads, membranes (including, but not limited to, nitrocellulose, cellulose, nylon, and glass wool), plastic and glass dishes or wells, etc.

The present invention is also directed to diagnostic and imaging methods for multiple myeloma and ovarian cancer using the monoclonal antibodies and binding fragments thereof as described hereinabove. Other cancers bearing the surface antigens of the invention are also amenable to these diagnostic procedures. The method involves administration or infusion of monoclonal antibodies or binding fragments as described herein, with or without conjugation to a detectable moiety, such as a radionuclide. After administration or infusion, the antibody, or antibody fragment, binds to the tumor cells, after which the location of the antibodies, or fragments, is detected. For detectably-labeled antibodies or their binding fragments, such as those labeled with a radionuclide, imaging instrumentation may be used to identify the location of the agent within the body. For use of unlabeled antibodies or fragments, a second, detectable reagent may be administered which locates the antibodies or antibody fragments, and thus may be suitably detected. These methods have been used for other antibodies, and the skilled artisan will be amply aware of these various methods for imaging the location of antibodies or fragments within the body.

In the case of ovarian cancer, as well as other cancers expressing the antigens described herein, the present invention is further directed to the diagnosis of cancer by the identification and measurement of shed cell surface glycoprotein in bodily fluids, such as blood, serum, or plasma. As ovarian cancer is a particularly difficult cancer to diagnose in its early stages, thus thwarting the opportunity for early treatment, methods for early diagnosis are particularly needed. Measurement of shed surface glycoprotein in a whole blood sample, for example, by use of an antibody, or fragment thereof, of the invention provides such early diagnosis and the opportunity for treatment. Such treatment may comprise the foregoing antibody-based therapy, in combination with other agents, or the use of such agents in the absence of the antibodies of the invention.

Furthermore, the level of shed ovarian cancer antigen measured in blood or other bodily fluids provides a means for monitoring the course of ovarian cancer therapy, including surgery, chemotherapy, radiation therapy, and the therapeutic methods of the present invention. By correlating the level of shed antigen with the severity of disease, the level of shed antigen can be used to indicate successful removal of the primary tumor and/or metastases, and the effectiveness of other therapies over time. A decrease in the level over time indicates a reduced tumor burden in the patient. In contrast, no change, or an increase in level, indicates ineffectiveness of therapy or the continued growth of the tumor.

The present invention is also directed to pharmaceutical compositions comprising a monoclonal antibody, or binding fragment thereof, which specifically binds to an antigen on the surface of a human myeloma cell, the antigen being further characterized as described hereinabove, together with a pharmaceutically-acceptable carrier or diluent. The invention is further directed to pharmaceutical compositions comprising a monoclonal antibody, or binding fragment thereof, including the monoclonal antibody produced from the hybridoma cell line deposited at the American Type Culture Collection having ATCC Accession No. PTA-450; antibodies that are capable of binding to the same antigenic determinant as does the monoclonal antibody produced by the hybridoma cell line deposited at the American Type Culture Collection having ATCC Accession No. PTA-450; binding fragments of the hybridoma cell line deposited at the American Type Culture Collection having ATCC Accession No. PTA-450; and binding fragments of a monoclonal antibody capable of binding to the same antigenic determinant as does the monoclonal antibody produced by the hybridoma cell line deposited at the American Type Culture Collection having ATCC Accession No. PTA-450; and a pharmaceutically-acceptable carrier, excipient, or diluent. Antibody fragments include but are not limited to F(ab')$_2$ fragments, Fab' fragments, Fv fragments, Fd' fragments, or Fd fragments.

A pharmaceutical composition includes a pharmaceutically acceptable carrier, excipient, or diluent. Preferably, the antibodies or binding fragments thereof are delivered parenterally, such as by intravenous administration. Alternative modes of administration include, but are not limited to, subcutaneous, intraperitoneal, oral, intranasal, intrathecal, rectal, of intramuscular administration, and the like. Suitable buffers, carriers, and other components known to those in the art are used in formulating a composition comprising the antibody, or fragments thereof, for suitable shelf-life and compatibility with administration. These substances may include ancillary agents such as buffering agents and protein stabilizing agents (e.g., polysaccharides).

The antibodies of the present invention are also useful for diagnostic applications, both in vitro and in vivo for the detection of human multiple myeloma and ovarian cancer cells that possess the antigen for which the antibodies are specific. In vitro diagnostic methods include immunohistological detection of tumor cells (e.g., on human tissue cells for excised tumor specimens), or serological detection of tumor-associated antigens (e.g., in blood samples or other biological fluids). Immunohistochemical techniques involve staining a biological specimen such as tissue specimen with the antibody of the invention and then detecting the presence of antibody complexed to its antigen as an antigen-antibody complex. The formation of such antibody-antigen complexes with the specimen indicates the presence of multiple myeloma cells in the tissue. Detection of the antibody on the specimen can be accomplished using techniques known in the art such as immunoenzymatic techniques, e.g., immunoperoxidase staining technique, or the avidin-biotin technique, or immunofluorescence techniques (see, e.g., Ciocca et al., "Immunohistochemical Techniques Using Monoclonal Antibodies", *Methods Enzymol,* 121:562-79, 1986 and Kimball, (ed), *Introduction to Immunology* ($2^{nd}$ Ed), pp. 113-117 (Macmillan Pub. Co., 1986).

Serologic diagnostic techniques involve the detection and quantification of tumor-associated antigens that have been secreted or "shed" into the serum or other biological fluids of patients thought to be suffering from multiple myeloma. Such antigens can be detected in the body fluids using techniques known in the art such as radioimmunoassay (RIA) or enzyme-linked immunoabsorbant assays (ELISA) wherein antibody reactive with the "shed" antigen is used to detect the presence of the antigen in a fluid sample (see, e.g., Uotila et al., "Two-Site Sandwich ELISA With Monoclonal Antibodies to Human AFP", *J. Immunol. Methods,* 42:11, 1981 and Allum et al., supra, at pp 48-51). Detection of the shed ovarian cancer antigen can be performed as described above.

Also as mentioned above, the antibodies of the present invention are useful for the measurement of shed ovarian cancer cell antigen in bodily fluids such as whole blood, serum, or plasma, for the diagnosis of ovarian cancer and the monitoring of the effectiveness of therapies.

In yet a further aspect of the present invention, monoclonal antibodies, or binding fragments thereof, having specificity for myeloma surface glycoprotein and ovarian cancer glycoprotein, as described, are labeled with a detectable moiety so that they can be used to diagnose or identify cells having the aforementioned antigens. Non-limiting examples of such labels include fluorophores, such as fluorescein isothiocyanate; chromophores, radionuclides, or enzymes. Such labeled antibodies or binding fragments may be used for the histological localization of the antigens, for ELISA, for cell sorting, and for other immunological techniques to detect and/or quantify the antigens, and cells bearing the antigens, for example. As noted above, a particular use of such labeled antibodies, or fragments thereof, is in determining the effectiveness of myeloma cell depletion from bone marrow tissue prior to transplant, particularly autologous bone marrow transplant.

EXAMPLES

The present invention may be better understood by reference to the following non-limiting Examples, which are provided as exemplary of the invention. The following examples are presented in order to more fully illustrate the preferred embodiments of the invention and should in no way be construed to limit the broad scope of the invention.

Example 1

Preparation and Screening of Hybridomas

1. Sources of cells Human myeloma cell lines (U266, OPM, RPMI1860, KR12 and NCI H929), and chronic myelogenic leukemic cell line (K562) were purchased from the American Type Culture Collection (ATCC®). Fresh human ovarian cancer, breast cancer, and liver cancer specimens were used. Cell lines of prostate cancer, LnCap (ATCC®); neuroblastoma cell line, NCI H2106 (ATCC®); and a cervical cancer, Caski (ATCC®) were also evaluated, as well as an EBV-transformed B cell tumor, Namalwa (ATCC®).

2. Immunization Mice were immunized with a pool of plasmacytoma cells, U266, RPMI1860 and OPM ($5 \times 10^6$ total in 50 µl containing Ribi adjuvant, 50%), in the left footpad, and with K562 cells ($5 \times 10^6$ total in 50 µl containing Ribi adjuvant, 50%) in the right footpad. The immunization was repeated after 14 days. The left popliteal lymph node was removed and the extracted cells were fused 3 days after the second immunization.

3. Generation of B cell hybridomas Monoclonal antibodies specific to multiple myeloma cells were produced by conventional methods. Popliteal (left) lymph node cells from immunized mice were fused with a mouse myeloma cell line (Sp2/0) in the presence of polyethylene glycol (PEG) to form hybridomas which were capable of producing monoclonal antibodies that specifically bound to human plasmacytoma cells.

4. Cellular ELISA—Flow cytometry analysis Various human tumor cell lines grown in in vitro culture were washed and stained with a panel of monoclonal antibodies selected on the basis of cellular ELISA screen. After 30 minutes of incubation on ice, the cells were washed and incubated with Rabbit anti-mouse IgG monoclonal antibody conjugated with fluorescein isothiocyanate (FITC). The mean intensity of the fluorescence was determined by flow cytometry using the FACScaliber (Becton and Dickinson). Histograms plotting the intensity of the staining correlated with cell count demonstrated the specificity of monoclonal antibody 69 (MA69) to human plasmacytoma cells.

5. Western blot analysis SDS-PAGE gels were prepared from stock solutions of 30% acylamide/0.8% bisacrylamide. TRIS-HCl/SDS, pH 8.8, sterile distilled $H_2O$, 10% (w/v) ammonium persulfate and TEMED were added, following standard procedures. A stacking gel was included if the samples were greater than 10 µl in volume. Surface membrane proteins from cells were prepared for electrophoresis by the following protocol: Cells from in vitro cultures were collected and washed. The cells were lysed following 3 repeated cycles of freeze-thaw (−80° C. and 37° C.). The lysates were stored at −20° C. until use. Membranes were prepared from cell lysates following a 30 minute centrifugation at 2500 rpm. The supernatant consisting of cytosolic protein and membranes was further separated by centrifugation at 40,000 rpm using an ultracentrifuge. The pellet containing the membrane fraction was collected and stored at −20° C.

Proteins were separated at 150 V for about 1.5 hours at 4° C. After separation, the proteins were transferred onto nitrocellulose in a Transfer box at 22 V run overnight at 4° C. The nitrocellulose was blocked using BLOTTO A® for 45 minutes at room temperature, reacted first with primary antibody for 45 minutes at room temperature, followed by washing and reaction with the appropriate secondary antibody conjugated to horseradish peroxidase. After washing, Amersham ECL reagents were used for detection.

The results of a first screen of B cell hybridomas generated from mice immunized as described above are shown in FIG. 1. The method of the screen was cellular ELISA which tested the binding of the supernatants removed from B cell hybridoma cultures to a pool of human plasmacytoma cells in one well, compared with their binding to human myelogenic leukemia cell line (K562), which served as a control. Net binding was calculated as the absorbance recorded for binding to the pool of human plasmacytoma cells after subtraction of binding to the K562 control cell line. In the initial screen, a pool of 4 hybridomas was tested in each well. Hybridoma pools that recorded high levels of differential binding were selected and then each hybridoma was tested individually.

No binding to cells from a fresh breast cancer tumor, a prostate cancer cell line, a neuroblastoma cell line, or a cervical cancer cell line was detected. In addition, no binding to an EBV-transformed B cell tumor was detected. FIG. 2 presents the results of selected hybridomas for the second screen. Hybridoma numbers 69, 75, and 194, i.e, MoAb 69, 75 and 194, showed specificity, compared with K562 cells.

In a further analysis of the above data, the net binding values (O.D.) obtained for the first screen compared with the second screen are shown in FIG. 3.

Example 2

Specificity Assessment of Monoclonal Antibodies

Cell surface staining using a panel of monoclonal antibodies Jul. 16, 1999 analyzed by flow cytometry is depicted in FIG. 4. A strong staining of plasmacytoma cells by MA69 (also called VAC69 herein) is demonstrated in panel F, while negative staining was demonstrated for the control cell lines, including human B cell tumor lines IM9 and HT (IM9 with isotype control, panel A; IM9 with MA69, panel B; HT with isotype control, panel C; HT with MA69, panel D) and myeloma cell line U266 with an isotype control monoclonal antibody (panel E). Furthermore, peripheral blood cells (PBMC) from normal individuals showed insignificant binding to the antibodies.

Hybridoma cell line IMM002.69.47.4 which produces monoclonal antibody MA69 was deposited on Aug. 3, 1999, with the American Type Culture Collection, 10801 University Boulevard, Manassas Va. 20110-2209, and has been assigned Accession No. PTA-450.

Example 3

Binding of Monoclonal Antibody to Cell Surface Glycoprotein

B cell hybridoma culture designated MA69 (also VAC69 herein) was shown to detect a distinct band on myeloma membranes from five human multiple myeloma cell lines (RPMI1860, U266, KR-12, OPM-1 and NCI H929) using Western blots. Four of the five myeloma cell lines showed binding to a cell surface glycoprotein with an approximate molecular weight of between about 78 and about 120 kDa. The PBMC serving as a negative control did not show binding to the antibody. In addition, no staining of two human B cell tumors (HT and IM9) was observed (FIG. 5).

Figure 5:
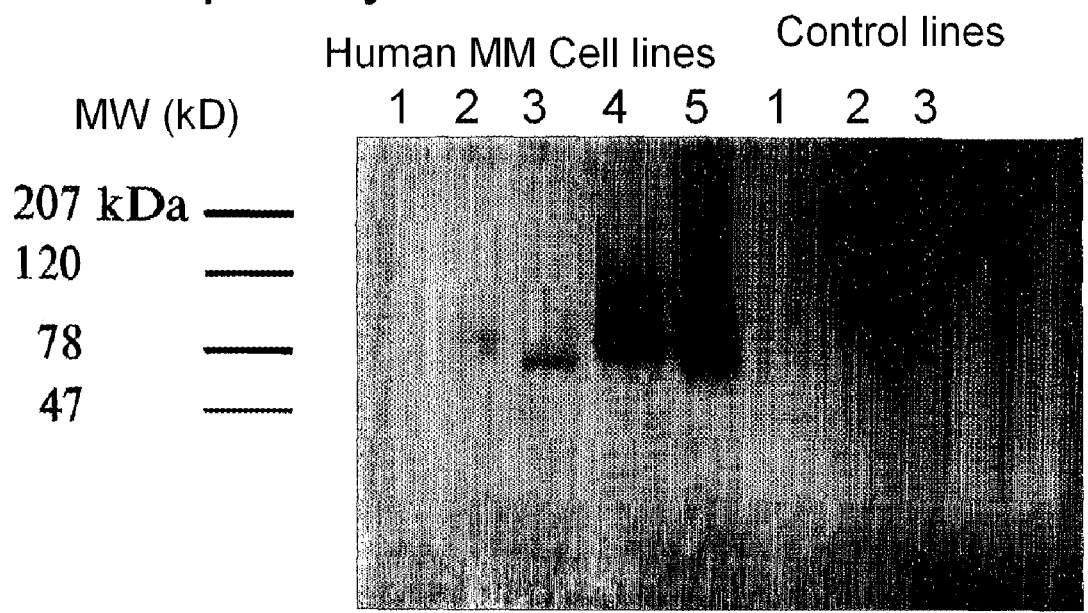
FIG. 5 represents further evaluation of the selected monoclonal antibodies using Western blot method, using membrane proteins extracted from five human myeloma cell lines tested individually, and controls, fractionated on SDS-PAGE.
Figure 6:
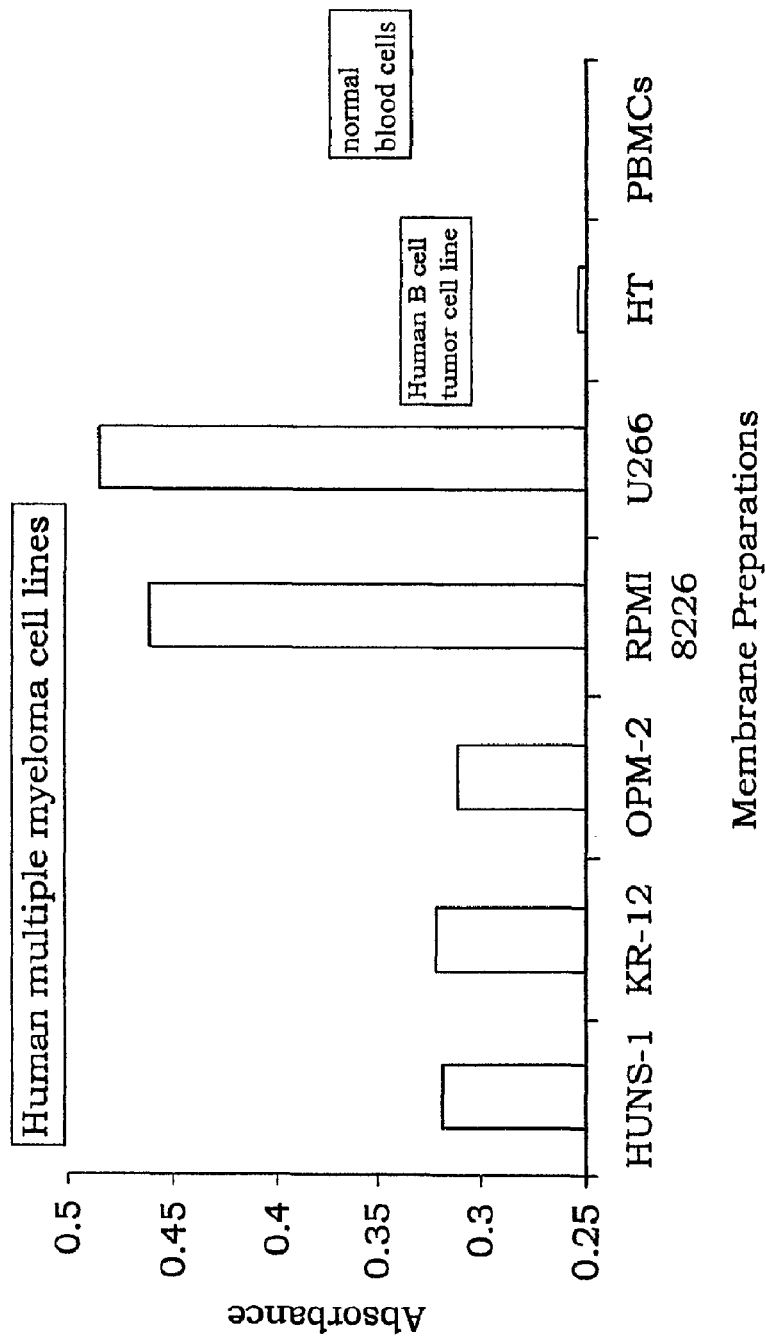
FIG. 6 presents results similar to those described for FIG. 5, using a cellular ELISA method.

FIG. 6 graphically presents the results of a repeat of the experiment described in FIG. 5 using a cellular ELISA method. In this experiment, the MA69 detected a distinct band in 5 out of 5 myeloma cell lines with varying intensities. The control membrane preparations consisting of normal PBMC and a human B cell tumor (HT) were not stained by the antibody.

Example 4

Detection of Shed Surface Glycoprotein from Cultured Myeloma Cells

Figure 7:
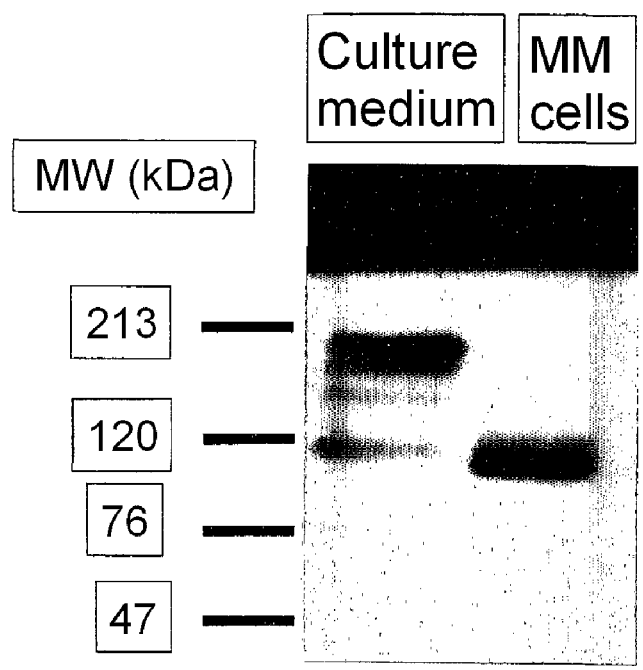
FIG. 7 shows an SDS-PAGE gel of concentrated culture fluid from multiple myeloma cells grown in serum-free medium for 5 days, blotted and probed with an antibody of the present invention.

Human myeloma cells were grown in AIM V serum-free medium for 5 days. The medium was collected and concentrated ten-fold using a Centricon device (Amersham). As a control, a cell lysate was prepared from MM cultured in vitro and fractionated by SDS-PAGE. Concentrated growth medium was fractionated coincidentally as a control. Blotting and probing with MA69 demonstrated the presence of the surface glycoprotein in the medium (FIG. 7, left lane).

These results show that VAC69-reactive glycoprotein was detectable in the growth medium of cultured MM. In addition, further experiments have demonstrated similar results for ovarian cancers. More specifically, VAC69-reactive glycoprotein was detectable in the growth medium of ovarian cancer cells and, more importantly, in the serum of ovarian cancer patients. Thus, VAC69 may be employed to detect the cancer-specific glycoprotein(s) in serum. An early screen for detection of ovarian cancer does not currently exist and would be useful in reducing the toll of fatalities inflicted by this malignancy.

Example 5

Surface Glycoprotein Present on the Surface of Human Ovarian Cancer Cells

Figure 8:
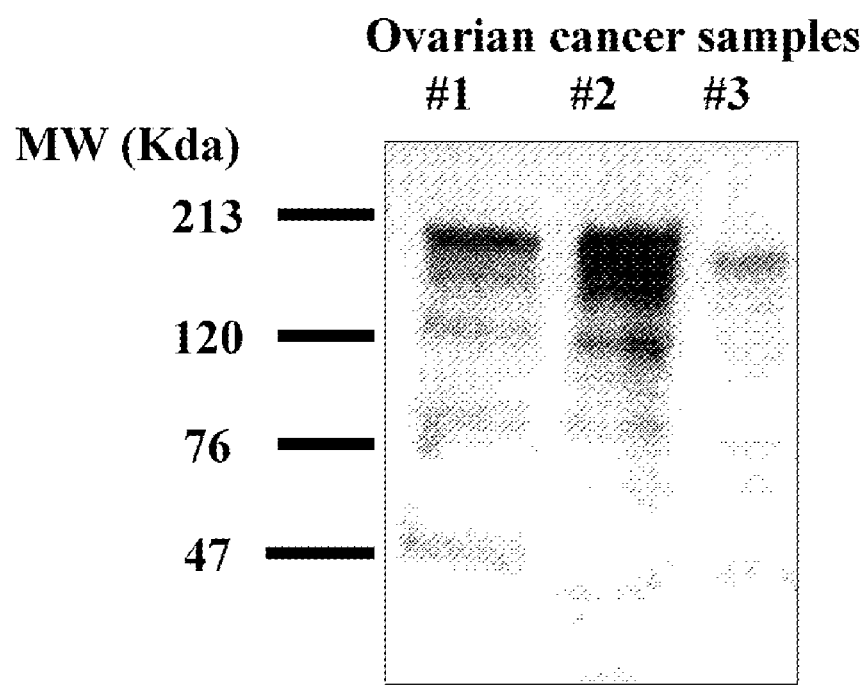
FIG. 8 depicts SDS-PAGE results of cell lysates from three ovarian cancer tumor cells from 3 patient. The tumor cells were digested with trypsin and homogenized. The gel was blotted and probed with an antibody of the present invention.

Three ovarian cancer tumors from three patients were digested with trypsin and homogenized. The cell lysates were fractionated by SDS-PAGE. The gel was blotted onto nitrocellulose (Western Blot) and probed with MA69 monoclonal antibody. As shown in FIG. 8, the surface glycoprotein of the invention is expressed on these cells. The antigen on ovarian cancer cells is a single glycosylated polypeptide with a molecular weight of about 76 kDa to about 213 kDa, as determined by SDS-PAGE under reducing conditions. The ovarian cancer cell antigen shares at least one epitope with the aforementioned multiple myeloma surface antigen.

Example 6

In vivo Adoptive Immunotherapy with the VAC69 Monoclonal Antibody of the Present Invention Induced the Obliteration of Established Tumors in SCID Mice The therapeutic potential of the VAC69 monoclonal antibody to treat ovarian carcinoma and MM was evaluated in SCID mice transplanted with human tumors, i.e., the human MM cell line (U266) or a primary culture established from a fresh ovarian tumor, (injected i.p. at 1×10⁶ cells per mouse). The tumor cells were allowed to proliferate and induce gross malignant ascites for seven days prior to initiation of treatment.

The mice were treated with 200 µg of the VAC69 monoclonal antibody, or an isotype-matched (IgG1) control, which were administered a total of nine times (3 times per week) over a three-week period. The control groups treated with isotype control developed large peritoneal tumors which incapacitated their movement and ability to feed; thus, these animals were consequently euthenized 14-16 days after the initiation of treatment. In others of the mice, tumor growth and survival rate were monitored. The experiment was terminated after 35 days.

The results of the adoptive immunotherapy experiments are presented in Tables 1-4 below. Tables 1 and 2 show the results of SCID mice that had received multiple myeloma cells and were subsequently treated with the VAC69 monoclonal antibody, or an isotype-matched control antibody, respectively, according to the present invention. Tables 3 and 4 show the results of SCID mice that had received ovarian tumor cells and were subsequently treated with the VAC69 monoclonal antibody, or an isotype-matched control antibody, respectively, according to the present invention. The results presented in Tables 1-4 indicate that 100% of the mice in the MM and ovarian carcinoma experimental groups had objective responses to treatment with VAC69. In the experimental groups, complete responses were noted in 60% (3/5) of mice that had received ovarian carcinoma cells (Table 3), and in 40% (2/5) of mice that had received MM cells (Table 1). These results indicate that VAC69 is cytotoxic to the tumor cells and is capable of curbing a rampant cancer, and, in some instances, completely eradicating an already established malignant tumor.

TABLE 1

MULTIPLE MYELOMA

| ANTIBODY | Mouse # | Ascites | Survival | Response |
|---|---|---|---|---|
| VAC69 | 1 | − | >35 | CR |
| VAC69 | 2 | − | >35 | CR |
| VAC69 | 3 | + | >35 | PR |
| VAC69 | 4 | ++ | >35 | PR |
| VAC69 | 5 | + | >35 | PR |

Objective Response, Table X: 100% (5/5); Partial Response (PR): 60% (3/5); Complete Response (CR): 40% (2/5)

TABLE 2

MULTIPLE MYELOMA - ISOTYPE-MATCHED CONTROL

| ANTIBODY | Mouse # | Ascites | Survival | Response |
|---|---|---|---|---|
| Isotype-matched control | 1 | +++ | 14 | NR |
| Isotype-matched control | 2 | +++ | 15 | NR |
| Isotype-matched control | 3 | +++ | 16 | NR |
| Isotype-matched control | 4 | +++ | 14 | NR |
| Isotype-matched control | 5 | +++ | 14 | NR |

Objective Response: 0% (0/5); No response (NR).

TABLE 3

OVARIAN CARCINOMA

| ANTIBODY | Mouse # | Ascites | Survival | Response |
|---|---|---|---|---|
| VAC69 | 1 | − | >35 | CR |
| VAC69 | 2 | − | >35 | CR |
| VAC69 | 3 | − | >35 | CR |
| VAC69 | 4 | ++ | >35 | PR |
| VAC69 | 5 | + | >35 | PR |

Objective Response: 100% (5/5); Partial Response (PR): 40% (2/5); Complete Response (CR): 60% (3/5).

TABLE 4

OVARIAN CARCINOMA - ISOTYPE-MATCHED CONTROL

| ANTIBODY | Mouse # | Ascites | Survival | Response |
|---|---|---|---|---|
| Isotype-matched control | 1 | +++ | 14 | NR |
| Isotype-matched control | 2 | +++ | 15 | NR |
| Isotype-matched control | 3 | +++ | 16 | NR |
| Isotype-matched control | 4 | +++ | 14 | NR |
| Isotype-matched control | 5 | +++ | 14 | NR |

Objective Response: 0% (0/5); No Response (NR).

Example 7

Analysis of the Performance of the Monoclonal Antibody of the Present Invention in Normal Human Tissues and Tumor Specimens Materials and Methods A. Source of Tissues Histologically normal human tissues and tumors were obtained from surgical and autopsy specimens. Fresh tissues were embedded in OCT compound (Miles Laboratories, Inc., Naperville, Ill.) in cryomolds, and snap-frozen in isopentane cooled by liquid nitrogen. Specimens were stored frozen at −80° C. until needed. At the time of analysis, the specimens were cut at 5 microns, placed on positively-charged slides, and air-dried.

Positive and negative control cell lines were used. U266, a human multiple myeloma cell line, (ATCC Accession No. TIB-196), served as a positive control, and IM9 (ATCC Accession No. CCL-159) and HT (ATCC Accession No. CRL-2260), two B cell lines, were used as negative controls.

B. Reagents

The VAC69 murine monoclonal antibody was characterized as described hereinabove. The species and antibody isotype were murine $IgG_{1/2a}$ at a concentration of 1.15 mg/ml. VAC69 was stored at −80° C. until needed. Once defrosted, it was stored at 2-8° C. The negative reagent control, murine $IgG_1$, was purchased from DAKO Corporation, Carpinteria, Calif., was supplied at a concentration of 0.1 mg/ml, and was stored at 2-8° C. The antibodies were diluted to working concentrations (as dictated by titration analyses) with Primary Antibody Diluent (Research Genetics, Huntsville, Ala.). The murine $IgG_1$ control was diluted to the same working concentration as was the VAC69 MoAb.

The reagent, cell line and specimen information is summarized in Table 5 below.

TABLE 5

| | |
|---|---|
| Test Article: | Murine IgG$_{1/2,4}$, VAC69 Monoclonal Antibody |
| Test Article Titer: | 5 μg/ml |
| Isotype Control: | Murine IgG$_1$ (DAKO Corp.) |
| Positive Specimen Control: | Human multiple myeloma cell line, U266, (ATCC Accession No. TIB-196) |
| Negative Specimen Controls: | Human B cell lines, IM9 and HT |

Table 5: All cells were provided in flasks with 50% viable cells per flask. The results described represent five repeat experiments.

C. Immunohistochemistry

Immunohistochemical studies were performed using an indirect peroxidase-conjugated immunohistochemical detection technique, called the DAKO Envision+™ System (DAKO Corporation, Carpinteria, Calif.), according to the manufacturer's instructions. Cryostat-cut sections were removed from the −80° C. freezer, and air-dried for 30 minutes. The slides were fixed in acetone for 5 minutes at 4° C. and then were washed in Phosphate Buffered Saline (PBS; Amresco, Solon, Ohio) at pH 7.2. Endogenous peroxidase activity was blocked with a 5-minute hydrogen peroxide solution, provided with the Envision+™ kit, followed by PBS washes. The slides were incubated with the VAC69 antibody or the isotype-matched control antibody for 30 minutes at room temperature, followed by PBS washes. Then, the slides were incubated with an anti-mouse antibody conjugated to a peroxidase-labeled dextran polymer, provided in the Envision+™ kit, for 30 minutes at room temperature. The slides were then washed in PBS. The peroxidase reaction was visualized by incubating for 5±1 minutes with 3,3'-diaminobenzidine-tetrahydrochloride substrate solution. The slides were thoroughly washed with tap water, counterstained with a modified Harris hematoxylin (American Master Tech. Scientific Inc., Lodi, Calif.), dipped in 0.25% acid alcohol, blued in 0.2% ammonia, dehydrated through graded alcohols, cleared in xylene, and coverslipped.

D. Controls

The positive control sections were derived from a frozen cell block prepared from the U266 cell line. The negative control sections were derived from frozen cell blocks prepared from the IM9 and HT cell lines described above.

The negative reagent control comprised the substitution of the primary antibody with an isotype-matched control antibody at the same antibody concentration as the test article. The negative control section refers to the tissue section to which the isotype control antibody was applied.

E. Interpretation of Slides

Interpretation of stained slides was performed by microscopic examination. In general, a morphologic review of the tissue on the slide determined whether an adequate amount of tissue was present, and whether the designated tissue was appropriately represented. Samples failing to meet the above standards were rejected from the analysis.

The scoring system included an analysis of staining intensity. The staining intensity of the test article was judged relative to the intensity of a control slide containing an adjacent section stained with an irrelevant, negative control antibody that was species- and isotype-matched to the test article. Staining of the section labeled with the negative reagent control was considered "background." A 0 indicated no staining relative to background, 1+ indicated minimal staining or a blush of stain, 2+ indicated moderately heavy staining, and 3+ indicated intensely heavy staining. In keeping with standard pathology practice, staining intensity was reported at the highest level of intensity observed.

F. Fixation Analyses

The rationale underlying fixation analysis is to select a fixative that allows for the highest percentage of positively staining cells, greatest staining intensity, and best morphological preservation.

A fixation analysis was performed using the positive and negative control cell lines, U266 and IM9, respectively. Of the fixatives evaluated (unfixed, acetone, ethanol, methanol/acetone, and 10% neutral buffered formalin), acetone for 5 minutes at 4° C. gave the best combination of morphological preservation and staining intensity.

G. Titration Analyses

The purpose of a titration analysis is to select the highest titer of VAC69 monoclonal antibody in order to detect antigen in tissues that may express low levels, but one that minimizes nonspecific binding. In addition, the test article titer is selected to ensure the highest combination of staining intensity and percentage of positively staining cells. Using acetone as the fixative, serial antibody dilutions (20 μg/ml to 1.25 μg/ml) were tested on the positive and negative target controls, U266 and IM9 cells, respectively. A concentration of 5 μg/ml of VAC69 gave the best results in terms of greatest percent of U266 cells staining, with the greatest staining intensity and without significant background staining. At this same concentration, no staining was observed in the IM9 cells.

The objective of the experiments described in this Example was to examine the expression of VAC69, a monoclonal antibody according to the present invention in a panel of normal tissues and tumors using indirect immunohistochemistry. This study was performed using Envision+™, (DAKO Corporation, Carpinteria, Calif.), which is a sensitive, biotin-free detection system. This system employs a dextran molecule to which a large number of peroxidase enzyme molecules and secondary antibodies are bound. The resulting polymeric conjugate offers increased sensitivity and minimized non-specific background staining. The sensitivity of this detection system allows the use of lower antibody titers and increases the signal to noise ratio.

TABLE 6

IMMUNOHISTOCHEMISTRY RESULTS OF VAC69 STAINING OF NORMAL HUMAN TISSUES

| TISSUE TYPE | Incidence | % Positive | Staining Intensity | Comment |
|---|---|---|---|---|
| Breast | 0/3 | 0 | 0 | Occasional Staining of Rare Histiocytes or Mononuclear Cells |
| Colon | 0/3 | 0 | 0 | Occasional Staining of Rare Histiocytes or Mononuclear Cells |
| Lung | 0/3 | 0 | 0 | Occasional Staining of Rare Histiocytes or Mononuclear Cells |
| Lymph Node | 2/3 | <10 | 3+ CM | Occasional |

TABLE 6-continued

IMMUNOHISTOCHEMISTRY RESULTS OF VAC69 STAINING OF NORMAL HUMAN TISSUES

| TISSUE TYPE | Incidence | % Positive | Staining Intensity | Comment |
|---|---|---|---|---|
|  |  |  | (plasma cells) | Staining of Rare Histiocytes or Mononuclear Cells |
| Ovary | 0/3 | 0 | 0 | Occasional Staining of Rare Histiocytes or Mononuclear Cells |
| Prostate | 0/3 | 0 | 0 | Occasional Staining of Rare Histiocytes or Mononuclear Cells |

TABLE 7

IMMUNOHISTOCHEMISTRY RESULTS OF VAC69 STAINING OF HUMAN TUMORS

| TISSUE TYPE | Incidence | % Positive | Staining Intensity | Comment |
|---|---|---|---|---|
| Multiple Myeloma | 3/3 | 80 | 3+ CM | Occasional Staining of Rare Histiocytes or Mononuclear Cells |
| Ovarian | 3/6 | 10-20 | 1-2+ CM | Occasional Staining of Rare Histiocytes or Mononuclear Cells |
| Prostate | 0/3 | 0 | 0 | Occasional Staining of Rare Histiocytes or Mononuclear Cells |
| Breast | 0/4 | 0 | 0 | Occasional Staining of Rare Histiocytes or Mononuclear Cells |
| Colon | 1/4 | 50 | 2+ CM | Occasional Staining of Rare Histiocytes or Mononuclear Cells |
| Non-SCLS | 2/3 | 20-40 | 1-2+ CM | Occasional Staining of Rare Histiocytes or Mononuclear Cells |

Fixation and titration analysis indicated that a 5-minute acetone fixation at 4° C. and a titer of 5 µg/ml provided the optimum results. U266 and IM9 cells were used as the positive and negative cell line controls, respectively. As expected, the U266 cells exhibited strong (3+) staining and the IM9 cells stained negatively in all cases.

A selection of normal human tissues was stained using the optimal fixation and titration (Table 6). Normal breast, colon, lung, lymph node, ovary, and prostate tissue samples did not exhibit significant staining, although one specimen of lymph node had weak (1+) staining of plasma cells. Moderate (2+) to strong (3+) staining of rare histiocytes and mononuclear cells was observed in some specimens. No staining was recorded for normal endothelium, smooth muscles, fibroblasts, stroma or nerve cells (see Table 6).

In addition to the normal tissues, four specimens of breast carcinoma, four specimens of colon carcinoma, three specimens of non-small cell lung carcinoma, three specimens of myeloma, six specimens of ovarian carcinoma, and three specimens of prostatic carcinoma were also tested (see Table 7). As observed in Table 7, no staining was observed in the tumor cell component of any of the breast or prostatic carcinoma specimens. Of the colon carcinoma specimens examined, one of four contained 50% moderately staining tumor cells, while the remaining specimens were negative. Of the non-small cell lung carcinoma cases examined, one of three contained 20% weakly staining tumor cells, a second case contained 40% moderately-staining tumor cells, while the third case was negative. Of the three myeloma specimens examined, all were positive, with 80% of the tumor cells staining with a strong intensity. Of the six ovarian carcinoma specimens examined, one contained less than 10% moderately staining tumor cells, a second contained about 20% moderately-staining tumor cells, and a third contained less than about 10% weakly-staining tumor cells; the remaining ovarian carcinoma specimens were negative. As with the normal tissue, moderate (2+) to strong (3+) staining of rare histiocytes and mononuclear cells was observed in some specimens.

In summary, monoclonal antibody VAC69 recognizes an antigen present in some colon, non-small cell lung and ovarian carcinoma samples tested, and in all myeloma samples tested. The antibody also recognizes plasma cells, histiocytes and mononuclear cells, which may reflect the presence of the same or a cross-reactive epitope on these cell types. That the antibody moderately stained about 20% of one ovarian carcinoma specimen and weakly stained about 10% of the cells of another is due to the presence of only a small number (%) of tumor cells in many cancer tissues, which are by-and-large composed of normal cells and sporadic numbers of tumor cells. In contrast, for MM, the population is monoclonal and accumulates in the bone marrow. Also, as will be appreciated by the skilled practitioner, ovarian cancer can be derived from diverse origins, e.g., fully differentiated or poorly- to moderately-differentiated, and also, from peritoneal tumors versus ovarian tumors. In addition, the VAC69 epitope for ovarian cancers may be sensitive to the fixation method used prior to staining the cells. Indeed, by Western Blot analysis, all four ovarian cancers tested expressed high levels of the VAC69 antigen. The results of Example 7 point to significant and specific staining of the specified tumor cell types by the VAC69 monoclonal antibody.

Example 8

Figure 9:
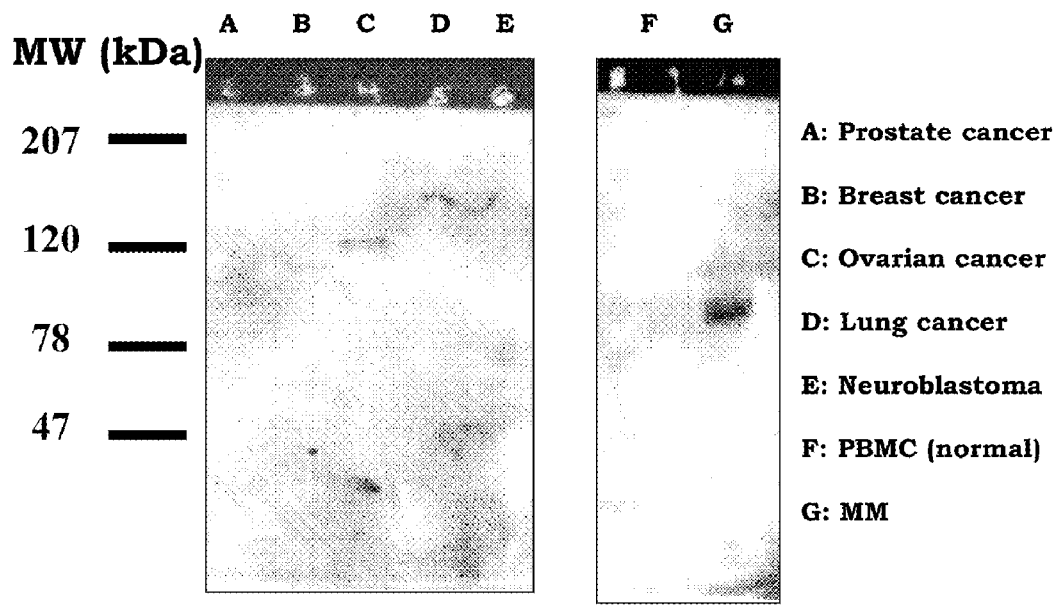
FIG. 9 shows the results of a Western Blot in which cellular lysates prepared from a prostate cancer cell line (LnCaP), breast cancer (fresh tumor), ovarian cancer (fresh tumor), lung cancer (fresh tumor), neuroblastoma (cell line), normal PBMC and a pool of human MM cell lines (RPMI-8226, U266, OPM-2, KR-12 and Huns-1) were fractionated by SDS-PAGE (8% gel). The gel was blotted onto nitrocellulose and incubated with VAC69 antibody. Note that what may appear as curved bands in lanes D (#5 on Blot) and E (#6 on Blot) are in fact a tear in the gel.

VAC69 Cross-Reacts with an Antigen Found in the Cell Membranes of Ovarian Carcinoma To further examine the cancer-specificity or tissue distribution of the VAC69 monoclonal antibody of the present invention, extracts from human prostate cancer, breast cancer, ovarian cancer, lung cancer, neuroblastoma, normal peripheral blood mononuclear cells (PBMC) and a pool of multiple myeloma (MM) cell lines were subjected to SDS-PAGE. The Western Blot scans presented in FIG. 9 show that the VAC69 MoAb failed to react with prostate cancer, breast cancer, lung cancer, or neuroblastoma extracts. In addition, immunohistochemical studies indicated the absence antibody binding to normal human tissues such as ovaries, prostate, lung, and colon (see Example 7), thus confirming the cancer-specificity of VA69. Moreover, a single chain molecule with a $M_r$ in the range of 78-120 kDa was detected in the lanes containing MM and ovarian cancer. The band visualized in ovarian cancer appears to be of a higher $M_r$, implying that this band may represent a distinct molecule expressing a communal epitope with the MM antigen.

Example 9

VAC69-Reactive Glycoprotein is Present on the Surface of Human Ovarian Fresh Tumors To determine the expression of the VAC69 monoclonal antibody in human ovarian cancer, three freshly excised ovarian carcinomas were digested with trypsin and homogenized. The resultant cell lysates were fractionated by SDS-PAGE. The gel was blotted and probed with VAC69 MoAb. As shown in FIG. 8 VAC69 reacted with all three ovarian tumors. The antigen expressed by ovarian cancer cells appears as a single high $M_r$ glycoprotein (around 200 kDa) or a set of glycoprotein bands with $M_r$ ranging from 76 kDa to 213 kDa. Since one ovarian tumor specimen expressed only the single high $M_r$ band, it is unlikely that the antigen consists of multiple subunits. Therefore, the lower $M_r$ bands may represent degradation products of the larger glycoprotein.

Example 10

VAC69 Induces In Vitro Cancer-Specific Cytotoxicity

To elucidate the ability of the VAC69 monoclonal antibody to kill cancer cells and to define the specificity of its cytotoxicity, cultures of human MM, chronic myelongenic leukemia (CML) cells, (K562), and B cell lymphoma cells (Namalwa) were incubated for one hour with VAC69 and complement. FIG. 10 shows that treatment with 10 μg/ml and 1 μg/ml of VAC69 resulted in the killing of 100% and 70%, respectively, of MM cells. Human lymphoma and leukemia cells were used as controls and were unaffected. VAC69 was also tested for its ability to induce tumor-specific killing of ovarian carcinoma cells. Incubation of ovarian carcinoma cells with complement and 10 μg/ml of VAC69 induced the killing of 50% of the cells following a 1 hour incubation with complement. Cytotoxicity controls displayed approximately 20% killing for complement alone and 0% killing for VAC69 alone. Thus, VAC69 was demonstrated to trigger cancer-specific killing of both ovarian cancer cells and multiple myeloma cells, results which parallel those of binding specificity.

The therapeutic effectiveness of VAC69 was demonstrated both in vitro (present Example) and in vivo (Example 6 above). Treatment with the VAC69 MoAb abrogated tumor growth and prolonged the survival of treated mice. Furthermore, treatment with VAC69 induced complete regression of large peritoneal tumors in 40% and 60% of SCID mice bearing human MM and ovarian cancer, respectively. Thus, VAC69 is cytotoxic to MM and ovarian cancer in its naked form without the aid of radioisotypes or toxins. The fact that VAC69 was effective in eradicating cancer in an animal model with advanced disease implies its potential for therapeutic intervention in human MM and ovarian cancers.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications, patents, references, and the like, are cited herein, the disclosures of which are incorporated herein by reference in their entireties.

What is claimed is:

1. A monoclonal antibody or fragment thereof which binds a cell surface glycoprotein antigen located on the surface of human multiple myeloma tumor cells, wherein said monoclonal antibody is produced by the hybridoma cell line deposited at the American Type Culture Collection having ATCC Accession No. PTA-450.

2. A monoclonal antibody or fragment thereof which binds a cell surface glycoprotein antigen located on the surface of human ovarian cancer cells, wherein said monoclonal antibody is produced by the hybridoma cell line deposited at the American Type Culture Collection having ATCC Accession No. PTA-450.

3. The fragment thereof according to claim 1, selected from the group consisting of a F(ab')2, a Fab', a Fv, a Fd', and a Fd.

4. A detectably labeled immunoconjugate comprising the monoclonal antibody or fragment thereof according to claim 1.

5. The detectably labeled immunoconjugate according to claim 4, wherein the monoclonal antibody or fragment thereof is labeled with a fluorophore, a chromophore, a radionuclide, or an enzyme.

6. An article of manufacture comprising a monoclonal antibody or fragment thereof according to claim 1 bound to a solid support.

7. A method of killing or inhibiting the growth of multiple myeloma tumor cells or ovarian cancer tumor cells expressing the antigen to which a monoclonal antibody produced by the hybridoma cell line deposited at the American Type Culture Collection having ATCC Accession No. PTA-450 specifically binds, comprising administering to a patient afflicted by multiple myeloma or ovarian cancer expressing said antigen the monoclonal antibody of claim 1 under conditions sufficient for binding the monoclonal antibody or binding fragment thereof to said multiple myeloma tumor cells or ovarian cancer tumor cells, thereby causing the death or growth inhibition of said multiple myeloma tumor cells or ovarian cancer tumor cells by the patient's immune cells.

8. A method of killing or inhibiting the growth of multiple myeloma tumor cells or ovarian cancer tumor cells expressing the antigen to which a monoclonal antibody produced by the hybridoma cell line deposited at the American Type Culture Collection having ATCC Accession No. PTA-450 specifically binds, comprising conjugating the monoclonal antibody or fragment thereof of claim 1 with a cytotoxic moiety capable of killing or inhibiting the growth of said multiple myeloma or ovarian cancer cells in the patient and administering the conjugate monoclonal antibody or fragment thereof and cytotoxic moiety to a patient afflicted by multiple myeloma or ovarian cancer expressing said antigen under conditions sufficient for binding said monoclonal antibody or binding fragment thereof to said multiple myeloma tumor cells or ovarian cancer tumor cells, thereby causing the death or growth inhibition of said multiple myeloma tumor cells or ovarian cancer tumor cells in the patient.

9. The method according to claim 8, wherein said cytotoxic moiety is a chemotherapeutic agent, a photo-activated toxin, or a radioactive agent.

10. A method of removing multiple myeloma cells expressing the antigen to which a monoclonal antibody produced by the hybridoma cell line deposited at the American Type Culture Collection having ATCC Accession No. PTA-450 specifically binds from an isolated cellular sample comprising the steps of exposing said cellular sample to a solid matrix on which the monoclonal antibody or fragment thereof of claim 1 is bound under conditions wherein said multiple myeloma cells adhere to said monoclonal antibody or fragment thereof and isolating a cellular fraction of said cellular sample which does not adhere to said solid matrix, thereby removing said multiple myeloma cells from said cellular sample.

11. The method according to claim 10, wherein said cellular sample from which said multiple myeloma cells are removed comprises bone marrow cells.

12. The method according to claim 11, wherein said cellular sample comprising bone marrow cells from which said multiple myeloma cells are removed is used for bone marrow transplant.

13. The method of claim 12, wherein said bone marrow transplant is an autologous bone marrow transplant.

14. A method killing or inhibiting the growth of multiple myeloma tumor cells or ovarian cancer tumor cells expressing the antigen to which a monoclonal antibody produced by the hybridoma cell line deposited at the American Type Culture Collection having ATCC Accession No. PTA-450 specifically binds in an isolated cellular sample comprising exposing said cellular sample to an immunoconjugate comprising the monoclonal antibody or fragment thereof of claim 1 conjugated with a cytotoxic moiety capable of killing or inhibiting the growth of said multiple myeloma or ovarian cancer cells under conditions sufficient for binding said monoclonal antibody or fragment thereof to said multiple myeloma tumor cells or ovarian cancer tumor cells, thereby causing the death or growth inhibition of said multiple myeloma tumor cells or ovarian cancer tumor cells in the sample.

15. The method according to claim 14, wherein said cytotoxic moiety is a chemotherapeutic agent, a photo-activated toxin or a radioactive agent.

16. A method of localizing multiple myeloma or ovarian cancer cells expressing the antigen to which a monoclonal antibody produced by the hybridoma cell line deposited at the American Type Culture Collection having ATCC Accession No. PTA-450 specifically binds in a patient comprising administering to the patient a detectably labeled immunoconjugate comprising a monoclonal antibody or fragment thereof of claim 1, wherein said detectably labeled monoclonal antibody or fragment thereof binds to said multiple myeloma or ovarian cancer cells within the patient, and locating said detectably labeled monoclonal antibody or fragment thereof within said patient, thereby localizing said multiple myeloma or ovarian cancer cells in said patient.

17. The method according to claim 16, wherein said detectably labeled immunoconjugate comprising a monoclonal antibody or fragment thereof of claim 1 is labeled with a fluorophore, a chromophore, a radionuclide, or an enzyme.

18. A pharmaceutical composition comprising the monoclonal antibody or fragment thereof of claim 1 and a pharmaceutically-acceptable carrier or diluent.

19. A chimeric version of the monoclonal antibody of claim 1, or an antigen binding fragment thereof, comprising the antigen binding site of said monoclonal antibody and the constant domains of a different antibody, which specifically binds to the same antigenic determinant of the cell surface glycoprotein antigen to which said monoclonal antibody binds.

20. A method of killing or inhibiting the growth of multiple myeloma tumor cells or ovarian cancer tumor cells expressing the antigen to which a monoclonal antibody produced by the hybridoma cell line deposited at the American Type Culture Collection having ATCC Accession No. PTA-450 specifically binds, comprising administering to a patient afflicted by multiple myeloma or ovarian cancer expressing said antigen an immunoconjugate comprising the monoclonal antibody or fragment thereof of claim 1 or the chimeric version thereof of claim 19, or an antigen binding fragment thereof, and a cytotoxic agent that is capable of killing or inhibiting the growth of said multiple myeloma or ovarian cancer cells in the patient under conditions sufficient for binding the monoclonal antibody or fragment thereof or the chimeric version or antigen binding fragment thereof to said multiple myeloma tumor cells or ovarian cancer tumor cells, thereby causing the death or growth inhibition of said multiple myeloma tumor cells or ovarian cancer tumor cells.

21. A method of killing or inhibiting the growth of multiple myeloma tumor cells or ovarian cancer tumor cells expressing the antigen to which a monoclonal antibody produced by the hybridoma cell line deposited at the American Type Culture Collection having ATCC Accession No. PTA-450 specifically binds, comprising administering to a patient afflicted by multiple myeloma or ovarian cancer expressing said antigen a composition comprising the monoclonal antibody of claim 1 or the chimeric version thereof of claim 20 under conditions sufficient for binding the monoclonal antibody or chimeric version thereof to said multiple myeloma tumor cells or ovarian cancer tumor cells, wherein said monoclonal antibody or chimeric antibody is capable of mediating complement mediated cytotoxicity to kill said multiple myeloma or ovarian cancer cells in the patient, thereby causing the death or growth inhibition of said multiple myeloma tumor cells or ovarian cancer tumor cells.

22. A method of killing or inhibiting the growth of multiple myeloma tumor cells or ovarian cancer tumor cells expressing the antigen to which a monoclonal antibody produced by the hybridoma cell line deposited at the American Type Culture Collection having ATCC Accession No. PTA-450 specifically binds, comprising administering to a patient afflicted by multiple myeloma or ovarian cancer expressing said antigen a composition comprising a chimeric version of the monoclonal antibody of claim 1 comprising the antigen binding site of said monoclonal antibody and the constant domains of a different antibody, wherein said chimeric version of the monoclonal antibody specifically binds to the same antigenic determinant of the cell surface glycoprotein antigen to which said monoclonal antibody binds and is capable of mediating antibody dependent cellular cytotoxicity or complement mediated cytotoxicity to kill said multiple myeloma or ovarian cancer cells in the patient, under conditions sufficient for binding the chimeric version to said multiple myeloma tumor cells or ovarian cancer tumor cells, thereby causing the death or growth inhibition of said multiple myeloma tumor cells or ovarian cancer tumor cells.

* * * * *